US006632831B2

(12) United States Patent
Hays et al.

(10) Patent No.: US 6,632,831 B2
(45) Date of Patent: Oct. 14, 2003

(54) BRANCHED CHAIN AMINO ACID-DEPENDENT AMINOTRANSFERASE INHIBITORS AND THEIR USE IN THE TREATMENT OF NEURODEGENERATIVE DISEASES

(75) Inventors: Sheryl Jeanne Hays, Ann Arbor, MI (US); Lain-Yen Hu, Ann Arbor, MI (US); Huangshu Lei, Ann Arbor, MI (US); Jeffrey David Scholten, Ann Arbor, MI (US); David Juergen Wustrow, Ann Arbor, MI (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/305,094

(22) Filed: Nov. 26, 2002

(65) Prior Publication Data

US 2003/0162779 A1 Aug. 28, 2003

Related U.S. Application Data

(60) Provisional application No. 60/333,593, filed on Nov. 27, 2001.

(51) Int. Cl.$^7$ .................... C07D 277/34; A61K 31/426

(52) U.S. Cl. ........................ 514/369; 548/184; 548/187

(58) Field of Search ................................ 548/184, 187; 514/369

(56) References Cited

U.S. PATENT DOCUMENTS

| | | | | |
|---|---|---|---|---|
| 4,775,677 A | * 10/1988 | Connor et al. | .............. | 514/369 |
| 5,290,800 A | 3/1994 | Cetenko et al. | ............. | 514/376 |
| 5,760,048 A | 6/1998 | Wang et al. | ................ | 514/290 |

FOREIGN PATENT DOCUMENTS

| | | |
|---|---|---|
| JP | 7-285952 | * 10/1995 |
| WO | 0142191 | 6/1991 |
| WO | 0224672 | 3/2002 |

OTHER PUBLICATIONS

Nagase, Chemical and Pharmaceutical Bulletin (19730, 21 (2) 270–8.*

PCT International Search Report, PCT/IB02/04727.

Toshio, "New Heterocyclic Derivative", *Patent Abstracts of Japan*, vol. 1996, No. 2, 1996.

Hutson et al., "Role of Branched–Chain Aminotransferase Isoenzymes and Gabapent in in Neurotransmitter Metabolism", *Journal of Neurochemistry*, vol. 71, No. 2, 1998, pp. 863–874.

* cited by examiner

*Primary Examiner*—Robert Gerstl

(74) *Attorney, Agent, or Firm*—P. C. Richardson; P. H. Ginsburg; R. L. Catania

(57) ABSTRACT

The invention relates to BCAT inhibitors and the use thereof for treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease and Down's syndrome, treating or preventing the adverse consequences of the overstimulation of the excitatory amino acids, treating anxiety, psychosis, convulsions, aminoglycoside antibiotics-induced hearing loss, migraine headache, chronic pain, neuropathic pain, Parkinson's disease, diabetic retinopathy, glaucoma, CMV retinitis, urinary incontinence, opioid tolerance or withdrawal, and inducing anesthesia, as well as for enhancing cognition.

15 Claims, No Drawings

BRANCHED CHAIN AMINO ACID-DEPENDENT AMINOTRANSFERASE INHIBITORS AND THEIR USE IN THE TREATMENT OF NEURODEGENERATIVE DISEASES

This application claims benefit of U.S. Provisional Application No. 60/333,593 filed Nov. 27, 2001.

FIELD OF THE INVENTION

This invention is related to branched chain amino acid-dependent amino transferase (BCAT) inhibitors. The invention is also directed to the use of BCAT inhibitors as neuro-protective agents for treating conditions such as stroke, cerebral ischemia, central nervous system trauma, hypoglycemia, anxiety, convulsions, aminoglycoside antibiotics-induced hearing loss, migraine headaches, chronic pain, neuropathic pain, glaucoma, CMV retinitis, diabetic retinopathy, psychosis, urinary incontinence, opioid tolerance or withdrawal, or neuro-degenerative disorders such as lathyrism, Alzheimer's disease, Parkinsonism, amyotrophic lateral sclerosis (ALS), and Huntington's Disease.

RELATED BACKGROUND ART

Excessive excitation by neurotransmitters can cause the degeneration and death of neurons. It is believed that this degeneration is in part mediated by the excitotoxic actions of the excitatory amino acids (EAA) glutamate and aspartate at the N-methyl-D-aspartate (NMDA) receptor. This excitotoxic action is considered responsible for the loss of neurons in cerebrovascular disorders such as cerebral ischemia or cerebral infarction resulting from a range of conditions, such as thromboembolic or hemorrhagic stroke, cerebral vasospasms, hypoglycemia, cardiac arrest, status epilepticus, perinatal asphyxia, anoxia such as from drowning, pulmonary surgery and cerebral trauma, as well as lathyrism, Alzheimer's disease, Parkinson's disease, and Huntington's disease.

Excitatory amino acid receptor antagonists that block NMDA receptors are recognized for usefulness in the treatment of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain and anxiety, and may be a significant causal factor in chronic neurodegenerative disorders such as Parkinson's disease (Klockgether T., Turski L., *Ann. Neurol.*, 1993;34:585–593), human immunodeficiency virus (HIV) related neuronal injury, amyotrophic lateral sclerosis (ALS), Alzheimer's disease (Francis P. T., Sims N. R., Procter A. W., Bowen D. M., *J. Neurochem.*, 1993;60(5):1589–1604, and Huntington's disease (see Lipton S., *TINS*, 1993;16(12):527–532; Lipton S. A., Rosenberg P. A., *New Eng. J. Med.*, 1994;330(9):613–622; and Bigge C. F., *Biochem. Pharmacol.*, 1993;45:1547–1561, and referenced cited therein.) NMDA receptor antagonists may also be used to prevent tolerance to opiate analgesia or to help control withdrawal symptoms from addictive drugs (Eur. Pat. Appl. 488,959A).

U.S. Pat. No. 5,352,683 discloses the treatment of chronic pain with a compound which is an antagonist of the NMDA receptor.

U.S. Pat. No. 4,902,695 discloses certain competitive NMDA antagonists that are useful for the treatment of neurological disorders, including epilepsy, stroke, anxiety, cerebral ischemia, muscular spasms, and neurodegenerative diseases such as Alzheimer's disease and Huntington's disease.

U.S. Pat. No. 5,192,751 discloses a method of treating urinary incontinence in a mammal which comprises administering an effective amount of a competitive NMDA antagonist.

SUMMARY OF THE INVENTION

The invention relates BCAT inhibitor compounds of Formula I

I

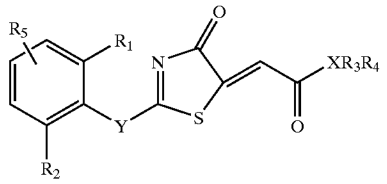

wherein:

X is N or O;

Y is NH or $CH_2$;

$R_1$ and $R_2$ are independently hydrogen, halogen or $C_1$–$C_3$ alkyl, with the proviso that both $R_1$ and $R_2$ cannot be hydrogen at the same time;

when X is N then $R_3$ and $R_4$ are independently hydrogen, alkyl, substituted alkyl, cycloalkyl, substituted cycloalkyl, alkenyl, substituted alkenyl, heterocyclyl, substituted heterocyclyl, arylalkyl, substituted arylalkyl, alkoxy, substituted alkoxy, arylalkoxy, or substituted arylalkoxy; or $R_3$ and $R_4$ together with X constitute a substituted or unsubstituted heterocyclyl group;

when X is O then $R_3$ is hydrogen, alkyl, substituted alkyl, cycloalkyl, substituted cycloalkyl, alkenyl, substituted alkenyl, heterocyclyl, substituted heterocyclyl, arylalkyl, substituted arylalkyl, alkoxy, substituted alkoxy, arylalkoxy, or substituted arylalkoxy and $R_4$ is absent; and $R_5$ is hydrogen or halogen;

where there is more than one stereoisomer, each chiral center may be independently R or S; or a pharmaceutically acceptable salt, ester, prodrug, or amide thereof.

The invention also relates to compounds of Formula I, wherein $R_5$ is hydrogen.

The invention also relates to compounds of Formula I, wherein $R_1$ is Cl.

The invention also relates to compounds of Formula I, wherein $R_1$ and $R_2$ are Cl.

The invention also relates to compounds of Formula I, wherein $R_1$ and $R_2$ are Cl and $R_5$ is hydrogen.

The invention also relates to compounds of Formula I, wherein $R_1$ is Cl, and X is O.

The invention also relates to compounds of Formula I, wherein $R_1$ and $R_2$ are Cl, X is 0 and $R_3$ is alkyl.

The invention also relates to compounds of Formula I, wherein $R_1$ and $R_2$ are Cl, X is N, $R_3$ is alkyl or cycloalkyl, and $R_4$ is hydrogen or alkyl, or $R_3$ and $R_4$ together with X constitute a pyrrolidine, piperidine, morpholine or N-alkylpiperazine ring.

The invention also relates to compounds of Formula I, wherein $R_1$ and $R_2$ are Cl, X is N, $R_3$ is alkyl, and $R_4$ is hydrogen.

The invention also relates to compounds selected from:

[2-(2,6-Dichloro-phenylamino)-4-oxo-4H-thiazol-5-ylidene]-acetic acid methyl ester;

[2-(2,6-Dichloro-phenylamino)-4-oxo-4H-thiazol-5-ylidene]-acetic acid ethyl ester;

[2-(2,6-Dichloro-phenylamino)-4-oxo-4H-thiazol-5-ylidene]-acetic acid tert-butyl ester;

[2-(2-Methyl-phenylamino)-4-oxo-4H-thiazol-5-ylidene]-acetic acid methyl ester;

[2-(2,6-Dichloro-phenylamino)-4-oxo-4H-thiazol-5-ylidene]-acetic acid;

[2-(2,6-Dichloro-phenylamino)-4-oxo-4H-thiazol-5-ylidene]-N-methyl-acetamide;

[2-(2,6-Dichloro-phenylamino)-4-oxo-4H-thiazol-5-ylidene]-N-ethyl-acetamide;

[2-(2,6-Dichloro-phenylamino)-4-oxo-4H-thiazol-5-ylidene]-N-propyl-acetamide;

[2-(2,6-Dichloro-phenylamino)-4-oxo-4H-thiazol-5-ylidene]-N-benzyl-acetamide;

[2-(2,6-Dichloro-phenylamino)-4-oxo-4H-thiazol-5-ylidene]-N-methoxy-acetamide;

[2-(2,4-Dichloro-phenylamino)-4-oxo-4H-thiazol-5-ylidene]-acetic acid methyl ester;

[2-(2,5-Dichloro-phenylamino)-4-oxo-4H-thiazol-5-ylidene]-acetic acid methyl ester;

[2-(2,3-Dichloro-phenylamino)-4-oxo-4H-thiazol-5-ylidene]-acetic acid methyl ester;

[2-(2,4,6-Trichloro-phenylamino)-4-oxo-4H-thiazol-5-ylidene]-acetic acid methyl ester;

[2-(2-Chloro-phenylamino)-4-oxo-4H-thiazol-5-ylidene]-acetic acid methyl ester;

2-[2-(2,6-Dichloro-phenylamino)-4-oxo-4H-thiazol-5-ylidene]-N-(2-methoxy-ethyl)-acetamide;

2-(2,6-Dichloro-phenylamino)-5-(2-oxo-2-piperidine-1-yl-ethylidene)-thiazol-4-one;

2-(2,6-Dichloro-phenylamino)-5-[2-(4-ethyl-piperazin-1-yl)-2-oxo-ethylidene)-thiazol-4-one;

2-[2-(2,6-Dichloro-phenylamino)-4-oxo-4H-thiazol-5-ylidene]-N-(3-pyrrolidin-1-yl-propyl)-acetamide;

2-[2-(2,6-Dichloro-phenylamino)-4-oxo-4H-thiazol-5-ylidene]-N-isopropyl-acetamide;

2-(2,6-Dichloro-phenylamino)-5-(2-oxo-2-pyrrolidin-1-yl-ethylidene)-thiazol-4-one;

N-Cyclohexyl-2-[2-(2,6-dichloro-phenylamino)-4-oxo-4H-thiazol-5-ylidene]-acetamide;

2-[2-(2,6-Dichloro-phenylamino)-4-oxo-4H-thiazol-5-ylidene]-N-(2,2-dimethoxy-ethyl)-acetamide;

2-(2,6-Dichloro-phenylamino)-5-[2-(3,5-dimethyl-piperidin-1-yl)-2-oxo-ethylidene)-thiazol-4-one;

2-(2,6-Dichloro-phenylamino)-5-[2-(3-dimethylamino-pyrrolidin-1-yl)-2-oxo-ethylidene)-thiazol-4-one;

2-[2-(2,6-Dichloro-phenylamino)-4-oxo-4H-thiazol-5-ylidene]-N-[2-(2-hydroxy-ethoxy)-ethyl]-acetamide;

2-[2-(2,6-Dichloro-phenylamino)-4-oxo-4H-thiazol-5-ylidene]-N-(3-methylsulfanyl-propyl)-acetamide;

2-[2-(2,6-Dichloro-phenylamino)-4-oxo-4H-thiazol-5-ylidene]-N-(2,3-dihydroxy-propyl)-acetamide;

2-[2-(2,6-Dichloro-phenylamino)-4-oxo-4H-thiazol-5-ylidene]-N-(2-methyl-allyl)-acetamide;

N-Cyclopentyl-2-[2-(2,6-dichloro-phenylamino)-4-oxo-4H-thiazol-5-ylidene]-acetamide;

N-Cyclopropylmethyl-2-[2-(2,6-dichloro-phenylamino)-4-oxo-4H-thiazol-5-ylidene]-N-propyl-acetamide;

2-[2-(2,6-Dichloro-phenylamino)-4-oxo-4H-thiazol-5-ylidene]-N-methyl-N-(1-methyl-pyrrolidin-3-yl)-acetamide;

2-[2-(2,6-Dichloro-phenylamino)-4-oxo-4H-thiazol-5-ylidene]-N-(2-phenoxy-ethyl)-acetamide;

2-[2-(2,6-Dichloro-phenylamino)-4-oxo-4H-thiazol-5-ylidene]-N-methyl-N-(8-methylamino-octyl)-acetamide;

N-(4-Chloro-benzyl)-2-[2-(2,6-dichloro-phenylamino)-4-oxo-4H-thiazol-5-ylidene]-acetamide;

N-(1-Benzyl-pyrrolidin-3-yl)-2-[2-(2,6-dichloro-phenylamino)-4-oxo-4H-thiazol-5-ylidene]-N-methyl-acetamide;

2-[2-(2,6-Dichloro-phenylamino)-4-oxo-4H-thiazol-5-ylidene]-N-(1,4-dimethyl-pentyl)-acetamide;

2-[2-(2,6-Dichloro-phenylamino)-4-oxo-4H-thiazol-5-ylidene]-N-(1,3-dimethyl-butyl)-acetamide; and N-Cycloheptyl-2-[2-(2,6-dichloro-phenylamino)-4-oxo-4H-thiazol-5-ylidene]-acetamide.

The invention also relates to a method of treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease, Parkinson's disease and Down's syndrome, treating or preventing the adverse consequences of the overstimulation of the excitatory amino acids, treating anxiety, psychosis, convulsions, chronic pain, neuropathic pain, diabetic retinopathy, glaucoma, CMV retinitis, urinary incontinence, and inducing anesthesia, as well as enhancing cognition, and preventing opiate tolerance and withdrawal symptoms, comprising administering to an animal in need of such treatment an effective amount of any one of the BCAT inhibitors of the present invention, or a pharmaceutically acceptable salt thereof.

The present invention also includes a pharmaceutical composition comprising a therapeutically effective amount of one or more compounds of Formula I and a pharmaceutically acceptable carrier.

DETAILED DESCRIPTION OF THE INVENTION

The present invention is predicated on the discovery that intraocular glutamate injection causes ganglion cell loss which is related to the early stages of diabetic retinopathy (Vorwerk et al., IOVS, 1996;37:1618–1624 and that an inhibitor of the branched chain amino acid-dependent aminotransferase pathway, specifically gabapentin, is effective in inhibiting the synthesis of glutamate (see example below), thus preventing diabetic retinopathy. Accordingly, the present invention provides a method for the prophylactic and therapeutic treatment of diabetic retinopathy, including treatment at the pre-diabetic retinopathy stage, the nonproliferative diabetic retinopathy stage, and the proliferative diabetic retinopathy stage. By "prophylactic" is meant the protection, in whole or in part, against diabetic retinopathy, in particular diabetic macular edema. By "therapeutic" is meant the amelioration of diabetic retinopathy, itself, and the protection, in whole or in part, against further diabetic retinopathy, in particular diabetic macular edema.

The method comprises the administration of an inhibitor of the branched chain amino acid-dependent aminotransferase pathway in an amount sufficient to treat the neurodegenerative disease or condition, for example, to treat the retina for retinopathy prophylactically or therapeutically. Any inhibitor of the branched chain amino acid-dependent aminotransferase pathway can be used in the method of the present invention as long as it is safe and efficacious. Herein, "branch chain amino acid-dependent aminotransferase (BCAT) inhibitor" will be used to refer to such compounds and is intended to encompass all compounds that affect the branch chain amino acid-dependent aminotransferase pathway at any and all points in the pathway.

Preferably, the BCAT inhibitor is a compound of Formula I as described above, or a pharmaceutically acceptable, BCAT pathway-inhibiting analogue or prodrug thereof or a pharmaceutically acceptable salt, ester, or amide of any of the foregoing.

Unless otherwise expressly stated, the following definitions are adhered to throughout this disclosure.

"Alkyl" means a straight or branched hydrocarbon radical having from 1 to 10 carbon atoms (unless stated otherwise) and includes, for example, methyl, ethyl, n-propyl, isopropyl, n-butyl, sec-butyl, isobutyl, tert-butyl, n-pentyl, iso-pentyl, n-hexyl, and the like. "Halogen" includes fluoro, chloro, bromo, and iodo.

"Alkenyl" means straight and branched hydrocarbon radicals having from 2 to 6 carbon atoms and one double bond and includes ethenyl, 3-buten-1-yl, 2-ethenylbutyl, 3-hexen-1-yl, and the like.

"Alkynyl" means straight and branched hydrocarbon radicals having from 2 to 6 carbon atoms and one triple bond and includes ethynyl, 3-butyn-1-yl, propynyl, 2-butyn-1-yl, 3-pentyn-1-yl, and the like.

"Cycloalkyl" means a monocyclic or polycyclic hydrocarbyl group such as cyclopropyl, cycloheptyl, cyclooctyl, cyclodecyl, cyclobutyl, adamantyl, norpinanyl, decalinyl, norbornyl, cyclohexyl, and cyclopentyl. Such groups can be substituted with groups such as hydroxy, keto, and the like. Also included are rings in which 1 to 3 heteroatoms replace carbons. Such groups are termed "heterocyclyl," which means a cycloalkyl group also bearing at least one heteroatom selected from O, S, or NR, where R is hydrogen, optionally substituted alkyl, optionally substituted alkenyl, optionally substituted cycloalkyl, optionally substituted heterocyclyl, optionally substituted aryl, optionally substituted arylalkyl or acyl, examples being substituted or unsubstituted oxiranyl, pyrrolidinyl, piperidyl, tetrahydropyran, piperazinyl, acylpiperazinyl, pyrrolidinyl, and morpholine.

"Alkoxy" refers to the alkyl groups mentioned above bound through oxygen, examples of which include methoxy, ethoxy, isopropoxy, tert-butoxy, and the like. In addition, alkoxy refers to polyethers such as $—O—(CH_2)_2—O—CH_3$, and the like.

"Alkanoyl" groups are alkyl linked through a carbonyl, ie, $C_1–C_5—C(O)—$. Such groups include formyl, acetyl, propionyl, butyryl, and isobutyryl.

"Acyl" means an alkyl or aryl (Ar) group bonded through a carbonyl group, ie, R—C(O)—. For example, acyl includes a $C_1–C_6$ alkanoyl, including substituted alkanoyl, wherein the alkyl portion can be substituted by $NR_6R_7$ or a carboxylic or heterocyclic group, where $R_6$ and $R_7$ are independently hydrogen, alkyl, cycloalkyl, alkenyl, heterocyclyl, substituted heterocyclyl or arylalkyl. Typical acyl groups include acetyl, benzoyl, and the like.

Where the alkyl groups described above are optionally substituted, the substituents are preferably 1 to 3 groups selected from $NR_6R_7$, phenyl, substituted phenyl, thio $C_1–C_6$ alkyl, $C_1–C_6$ alkoxy, hydroxy, hydroxyalkoxy, carboxy, $C_1–C_6$ alkoxycarbonyl, halo, nitrile, cycloalkyl, and a 5- or 6-membered carbocyclic ring or heterocyclic ring having 1 or 2 heteroatoms selected from nitrogen, substituted nitrogen, oxygen, and sulfur. "Substituted nitrogen" means nitrogen bearing $C_1–C_6$ alkyl or $(CH_2)nPh$ where n is 1, 2, or 3. Perhalo and polyhalo substitution is also embraced.

Examples of substituted alkyl groups include 2-aminoethyl, pentachloroethyl, trifluoromethyl, 2-diethylaminoethyl, 2-dimethylaminopropyl, ethoxycarbonylmethyl, 3-phenylbutyl, methanylsulfanylmethyl, methoxymethyl, 3-hydroxypentyl, 2-carboxybutyl, 4-chlorobutyl, 3-cyclopropylpropyl, pentafluoroethyl, 3-morpholinopropyl, piperazinylmethyl, and 2-(4-methylpiperazinyl)ethyl.

Further, examples of substituted alkyl groups include dimethylaminomethyl, carboxymethyl, 4-morpholinobutyl, 4-tetrahydropyrinidylbutyl, 3-imidazolidin-1-ylpropyl, 4-tetrahydrothiazol-3-yl-butyl, phenylmethyl, 3-chlorophenylmethyl, and the like.

The term "aryl" refers to unsubstituted and substituted aromatic groups. Heteroaryl groups have from 4 to 9 ring atoms, from 1 to 4 of which are independently selected from the group consisting of O, S, and N. Preferred heteroaryl groups have 1 or 2 heteroatoms in a 5- or 6-membered aromatic ring. Mono and bicyclic aromatic ring systems are included in the definition of aryl and heteroaryl. Typical aryl and heteroaryl groups include phenyl, 3-chlorophenyl, 2,6-dibromophenyl, pyridyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, pyrrole, pyrazole, imidazole, thiazole, and the like.

Preferred aryl groups are phenyl and phenyl substituted by 1, 2, or 3 groups independently selected from the group consisting of alkyl, alkoxy, thio, thioalkyl, hydroxy, $—COOR_8$, amino of the formula $—NR_6R_7$, and $T(CH_2)_mQR_6$ or $T(CH_2)_mCO_2R_6$ wherein m is 1 to 6, T is O, S, $NR_6$, $N(O)R_6$, or $CR_6R_7$, Q is O, S, $NR_7$, $N(O)R_7$, wherein $R_6$ and $R_7$ are as described above, and $R_8$ is alkyl or substituted alkyl, for example, methyl, trichloroethyl, diphenylmethyl, and the like. The alkyl and alkoxy groups can be substituted as defined above. For example, typical groups are carboxyalkyl, alkoxycarbonylalkyl, hydroxyalkyl, hydroxyalkoxy, and alkoxyalkyl.

The symbol "—" means a bond.

The term "patient" means all animals including humans. Examples of patients include humans, cows, dogs, cats, goats, sheep, and pigs.

The compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds of Formula I are capable of further forming both pharmaceutically acceptable formulations comprising salts, esters, amides, and prodrugs. As used herein, the term "pharmaceutically acceptable salts, esters, amides, and prodrugs" refers to those carboxylate salts, amnino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed and including, but not limited to, acid addition and/or base salts, solvents and N-oxides of a compound of Formula I. This invention also provides pharmaceutical formulations comprising a compound of Formula 1 together with a pharmaceutically acceptable carrier, diluent, or excipient therefor. All of these forms are within the present invention.

Pharmaceutically acceptable acid addition salts of the compounds of Formula I include salts derived form inorganic acids such as hydrochloric, nitric, phosphoric, sulfuric, hydrobromic, hydriodic, phosphorus, and the like, as well as the salts derived from organic acids, such as aliphatic mono-and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge et al., "Pharmaceutical Salts," *J. of Pharmaceutical Science*, 1977;66:1–19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge et al., supra., 1977.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines, and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above Formulae, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference. In general, a prodrug is a drug which has been chemically modified and may be biologically inactive at its site of action, but which may be degraded or modified by one or more enzymatic or other in vivo processes to the parent bioactive form.

A therapeutically effective amount is an amount of a compound of Formula I that when administered to a patient, ameliorates a symptom of the disease.

The BCAT inhibitor, which is preferably a compound of Formula I, a BCAT pathway-inhibiting analogue of Formula I, a BCAT pathway-inhibiting prodrug of Formula I, or a pharmaceutically acceptable salt of any of the foregoing, can be administered in accordance with the present inventive method by any suitable route. Suitable routes of administration include systemic, such as orally or by injection, topical, intraocular, periocular (e.g., subTenon's), subconjunctival, subretinal, suprachoroidal and retrobulbar. The manner in which the BCAT inhibitor is administered is dependent, in part, upon whether the treatment of retinopathy is prophylactic or therapeutic. The manner in which the BCAT inhibitor is administered for therapeutic treatment of retinopathy is dependent, in part, upon the cause of the retinopathy.

For example, given that diabetes is the leading cause of retinopathy, the BCAT inhibitor can be administered prophylactically as soon as the pre-diabetic retinopathy state is detected. For the prophylactic treatment of retinopathy that can result from diabetes, the BCAT inhibitor is preferably administered systemically, e.g., orally or by injection. For the therapeutic treatment of nonproliferative diabetic retinopathy, the BCAT inhibitor can be administered systemically, e.g., orally or by injection, or intraocularly. Proliferative diabetic retinopathy can be therapeutically treated by the administration of the BCAT inhibitor intraocularly, topically, subconjunctivally or periocularly (e.g., subTenon's), for example. The BCAT inhibitor is preferably administered intraocularly, topically, subconjunctivally or periocularly (e.g., subTenon's) for the prophylactic or therapeutic treatment of retinopathy before, during or after surgical removal from an eye of scar tissue generated during neovascularization during the proliferative diabetic stage.

The BCAT inhibitor is preferably administered as soon as possible after it has been determined that an animal, such as a mammal, specifically a human, is at risk for retinopathy (prophylactic treatment) or has begun to develop retinopathy (therapeutic treatment). Treatment will depend, in part, upon the particular BCAT inhibitor used, the amount of the BCAT inhibitor administered, the route of administration, and the cause and extent, if any, of retinopathy realized.

One skilled in the art will appreciate that suitable methods of administering a BCAT inhibitor, which is useful in the present inventive methods, are available. Although more than one route can be used to administer a particular BCAT inhibitor, a particular route can provide a more immediate and more effective reaction than another route. Accordingly, the described routes of administration are merely exemplary and are in no way limiting.

The dose administered to an animal, particularly a human, in accordance with the present invention should be sufficient to effect the desired response in the animal over a reasonable time frame. One skilled in the art will recognize that dosage will depend upon a variety of factors, including the strength of the particular BCAT inhibitor employed, the age, species, condition or disease state, and body weight of the animal, as well as the amount of the retina about to be affected or actually affected by retinopathy. The size of the dose also will be determined by the route, timing and frequency of administration as well as the existence, nature, and extent of any adverse side effects that might accompany the administration of a particular BCAT inhibitor and the desired physiological effect. It will be appreciated by one of ordinary skill in the art that various conditions or disease states, in particular, chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. The present inventive method will typically involve the administration of from about 1 mg/kg/day to about 100 mg/kg/day, preferably from about 15 mg/kg/day to about 50 mg/kg day, if administered systemically. Intraocular administration typically will involve the administration of from about 0.1 mg total to about 5 mg total, preferably from about 0.5 mg total to about 1 mg total. A preferred concentration for topical administration is 100 mu M.

Compositions for use in the present inventive method preferably comprise a pharmaceutically acceptable carrier and an amount of a BCAT inhibitor sufficient to treat retinopathy prophylactically or therapeutically. The carrier can be any of those conventionally used and is limited only by chemico-physical considerations, such as solubility and lack of reactivity with the compound, and by the route of administration. It will be appreciated by one of ordinary skill in the art that, in addition to the following described pharmaceutical compositions, the BCAT inhibitor can be formulated as polymeric compositions, inclusion complexes, such as cyclodextrin inclusion complexes, liposomes, microspheres, microcapsules and the like (see, e.g., U.S. Pat. Nos. 4,997,652; 5,185,152; and 5,718,922).

The BCAT inhibitor can be formulated as a pharmaceutically acceptable acid addition salt. Examples of pharmaceutically acceptable acid addition salts for use in the pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulphonic, for example p-toluenesulphonic, acids.

The pharmaceutically acceptable excipients described herein, for example, vehicles, adjuvants, carriers or diluents, are well-known to those who are skilled in the art and are readily available to the public. It is preferred that the pharmaceutically acceptable carrier be one which is chemically inert to the BCAT inhibitor and one which has no detrimental side effects or toxicity under the conditions of use.

The choice of excipient will be determined in part by the particular BCAT inhibitor, as well as by the particular method used to administer the composition. Accordingly, there is a wide variety of suitable formulations of the pharmaceutical composition of the present invention. The following formulations are merely exemplary and are in no way limiting.

Injectable formulations are among those that are preferred in accordance with the present inventive method. The requirements for effective pharmaceutically carriers for injectable compositions are well-known to those of ordinary skill in the art (see Pharmaceutics and Pharmacy Practice, J. B. Lippincott Co., Philadelphia, Pa., Banker and Chalmers, eds., pages 238–250 (1982), and ASHP Handbook on Injectable Drugs, Toissel, 4th ed., pages 622–630 (1986). It is preferred that such injectable compositions be administered intramuscularly, intravenously, or intraperitoneally.

Topical formulations are well-known to those of skill in the art. Such formulations are suitable in the context of the present invention for application to the skin. The use of patches, corneal shields (see, e.g., U.S. Pat. No. 5,185,152), and ophthalmic solutions (see, e.g., U.S. Pat. No. 5,710,182) and ointments, e.g., eye drops, is also within the skill in the art.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The effectiveness of an orally administered drug is dependent upon the drug's efficient transport across the mucosal epithelium and its stability in entero-hepatic circulation. Drugs that are effective after parenteral administration but less effective orally, or whose plasma half-life is considered too short, may be chemically modified into a prodrug form.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inhibitor can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride, with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants. Oils, which can be used in parenteral formulations include petroleum, animal, vegetable, or synthetic oils. Specific examples of oils include peanut, soybean, sesame, cottonseed, corn, olive, petrolatum, and mineral.

Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metals, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-p-aminopropionates, and 2-alkyl-imidazoline quaternary ammonium salts, and (e) mixtures thereof.

The parenteral formulations will typically contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17.

The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Such compositions can be formulated as intraocular formulations, sustained-release formulations or devices (see, e.g., U.S. Pat. No. 5,378,475). For example, gelantin, chondroitin sulfate, a polyphosphoester, such as bis-2-hydroxyethyl-terephthalate (BHET), or a polylactic-glycolic acid (in various proportions) can be used to formulate sustained-release formulations. Implants (see, e.g., U.S. Pat. Nos. 5,443,505; 4,853,224; and 4,997,652), devices (see, e.g., U.S. Pat. Nos. 5,554,187; 4,863,457; 5,098,443; and 5,725,493), such as an implantable device, e.g., a mechanical reservoir, an intraocular device or an extraocular device with an intraocular conduit (e.g., 100 mu–1 mm in diameter), or an implant or a device comprised of a polymeric composition as described above, can be used.

The present inventive method also can involve the co-administration of other pharmaceutically active compounds. By "co-administration" is meant administration before, concurrently with, e.g., in combination with the BCAT inhibitor in the same formulation or in separate formulations, or after administration of a BCAT inhibitor as described above. For example, corticosteroids, e.g., prednisone, methylprednisolone, dexamethasone, or triamcinalone acetinide, or noncorticosteroid anti-inflammatory compounds, such as ibuprofen or flubiproben, can be co-administered. Similarly, vitamins and minerals, e.g., zinc, antioxidants, e.g., carotenoids (such as a xanthophyll carotenoid like zeaxanthin or lutein), and micronutrients can be co-administered. A general synthetic scheme for preparing compounds of Formula I is shown on Scheme 1.

Scheme 1

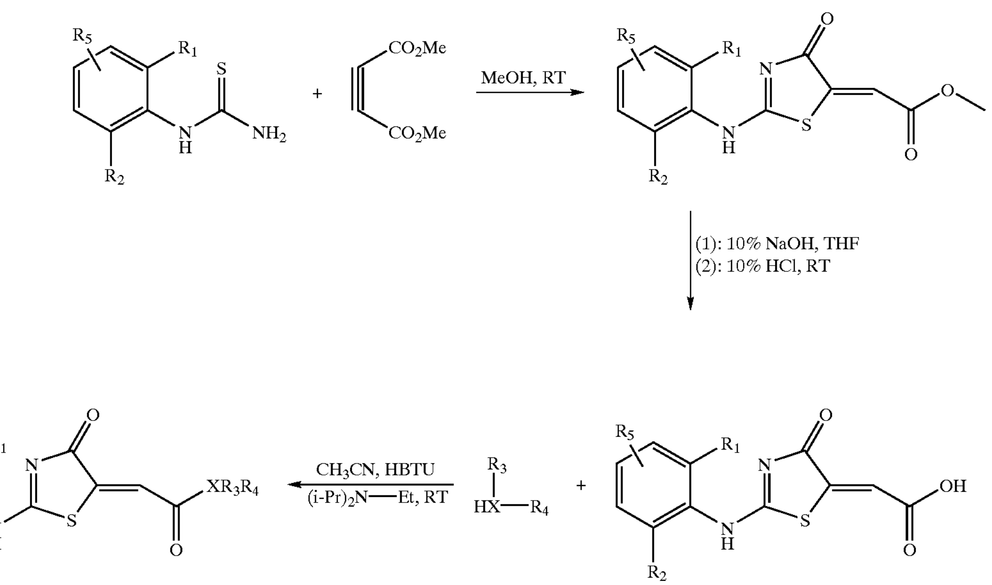

EXAMPLE 1

[2-(2,6-Dichloro-phenylamino)-4-oxo-4H-thiazol-5-ylidene]-acetic Acid Methyl Ester

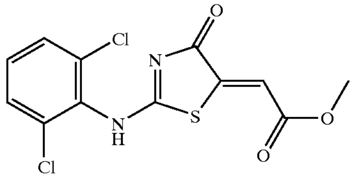

2,6-Dichlorophenylthiourea (3.0 g, 13.6 mmol) was dissolved in 50 mL of dry methanol and dimethyl acetylenedicarboxylate (13.8 mmol, 1.7 mL) was added over a 10-minute period. The mixture was stirred at 25° C. for 40 minutes, then the mixture was heated at 55° C. for 3 hours. The solvent was removed by rotvap, and the crude product was recrystallized from methanol to yield the desired product.

MS: 332.9 (M+1 for $C_{12}H_8Cl_2N_2O_3S$), TLC: $SiO_2$, $R_f$=0.38 (2:1 hexane/EtOAc). Mp: 189.1–189.7° C., HPLC: C-18 Column ($H_2O/CH_3CN$=1:1 with 0.1% TFA), RT Time 6.0 minutes, Purity: 94.62%. Analysis ($C_{12}H_8Cl_2N_2O_3S$): (calc) C: 43.52, H: 2.43, N: 8.46, (found) C: 43.50, H: 2.34, N: 8.38; $^1$H NMR (400 MHz, $CDCl_3$) δ 3.78 (s, 3H), 6.90 (s, 1H), 7.06 (t, 1H, J=5.9 Hz), 7.33 (d, 2H, J=5.6 Hz), 13.17 (s, 1H).

EXAMPLE 2

[2-(2,6-Dichloro-phenylamino)-4-oxo-4H-thiazol-5-ylidene]-acetic Acid Ethyl Ester

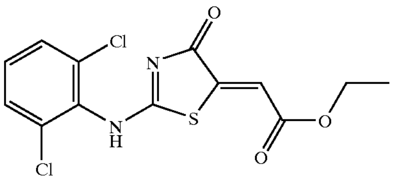

Example 2 was synthesized in accordance with the methods of Example 1, except that diethyl acetylenedicarboxylate was used instead of the dimethyl acetylenedicarboxylate. The desired product was recrystallized from methanol to yield a yellow crystal (97% yield).

MS: 346.9 (M+1 for $C_{13}H_{10}Cl_2N_2O_3S$), TLC: $SiO_2$, $R_f$=0.80 (1:1 hexane/EtOAc). Mp: 185.0–185.8° C., HPLC: C-18 Column ($H_2O/CH_3CN$=1:1 with 0.1% TFA), RT Time 13.1 minutes, Purity: 98.15%. Analysis ($C_{13}H_{10}Cl_2N_2O_3S$): (calc) C: 45.23, H: 2.92, N: 8.11, (found) C: 44.98, H: 2.75, N: 8.01; $^1$H NMR (400 MHz, $CDCl_3$) δ 1.18 (t, 3H, J=7.5 Hz), 4.15 (q, 2H, J=6.6 Hz), 6.71 (s, 1H), 7.20 (t, 1H, J=7.3 Hz), 7.52 (d, 2H, J=8.1 Hz), 13.17 (s, 1H).

EXAMPLE 3

[2-(2,6-Dichloro-phenylamino)-4-oxo-4H-thiazol-5-ylidene]-acetic Acid Tert-butyl Ester

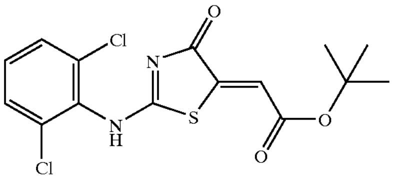

Example 3 was synthesized in accordance with the methods of Example 1, except that di-tert-butyl acetylenedicarboxylate was used instead of the dimethyl acetylenedicarboxylate. The desired product was recrystallized from methanol to yield a white crystal (95% yield).

MS: 374.9 (M+1 for $C_{15}H_{14}Cl_2N_2O_3S$), TLC: $SiO_2$, $R_f$=0.81 (1:1 hexane/EtOAc). Mp: >230° C., HPLC: C-18 Column ($H_2O/CH_3CN$=1/1 with 0.1% TFA), RT Time 26.1 minutes, Purity: 98.93%. Analysis ($C_{15}H_{14}Cl_2N_2O_3S$): (calc) C: 48.27, H: 3.78, N: 7.51, (found) C: 47.68, H: 3.49, N: 7.39; $^1$H NMR (400 MHz, $CDCl_3$) δ 1.38 (s, 9H), 6.59 (s, 1H), 7.18 (t, 1H, J=7.3 Hz), 7.52 (d, 2H, J=8.1 Hz), 13.15 (s, 1H).

EXAMPLE 4

[2-(2-Methyl-phenylamino)-4-oxo-4H-thiazol-5-ylidene]-acetic Acid Methyl Ester

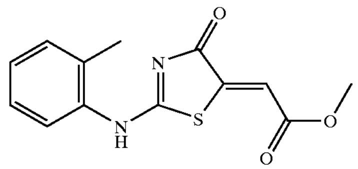

Example 4 was synthesized in accordance with the methods of Example 1, except that 2-methylphenylthiourea was used instead of the 2,6-dichlorophenylthiourea. The desired product was recrystallized from ethyl acetate to yield a yellow crystal (92% yield).

MS: 277.0 (M+1 for $C_{13}H_{12}N_2O_3S$), TLC: $SiO_2$, $R_f$=0.69 (1:1 hexane/EtOAc). Mp: 200.7–201.2° C., HPLC: C-18 Column ($H_2O/CH_3CN$=1/1 with 0.1% TFA), RT Time 5.61 minutes, Purity: 99.75%. Analysis ($C_{13}H_{12}N_2O_3S$): (calc) C: 56.51, H: 4.38, N: 10.14, (found) C: 56.58, H: 4.35 N: 9.96; $^1$H NMR (400 MHz, $CDCl_3$) δ 2.09 (s, 3H), 3.68 (s, 3H), 6.69 (s, 1H), 7.18–7.30 (m, 4H), 12.65 (s, 1H).

EXAMPLE 5

[2-(2,6-Dichloro-phenylamino)-4-oxo-4H-thiazol-5-ylidene]-acetic Acid

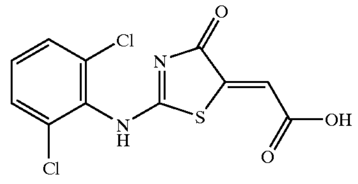

A reaction mixture of [2-(2,6-dichloro-phenylamino)-4-oxo-4H-thiazol-5-ylidene]-acetic acid methyl ester (3 g, Example 1), NaOH (1N in $H_2O$, 30 mL), THF (20 mL) was heated to 40° C. and stirred for 48 hours. The mixture was acidified to PH=1 by adding 10% aqueous HCl. Then the mixture was extracted with ethyl acetate (25 mLx3). The organic extracts were dried over $MgSO_4$, filtered, concentrated, and dried under vacuum to yield the desired product as a white solid.

MS: 317.9 (M+1 for $C_{11}H_6Cl_2N_2O_3S$), TLC: $SiO_2$, $R_f$=0.10 (1:1 hexane/EtOAc). Mp: >230° C., $^1$H NMR (400 MHz, $CDCl_3$) δ 6.66 (s, 1H), 7.18 (t, 1H, J=7.3 Hz), 7.52 (d, 2H, J=8.1 Hz), 13.15 (s, 1H).

EXAMPLE 6

[2-(2,6-Dichloro-phenylamino)-4-oxo-4H-thiazol-5-ylidene]-N-methyl-acetamide

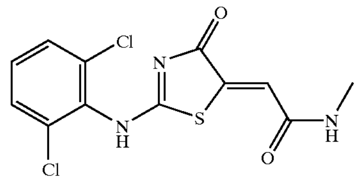

[2-(2,6-Dichloro-phenylamino)-4-oxo-4H-thiazol-5-ylidene]-acetic acid (0.1 g, 0.3 mmol, Example 5) was suspended in 5 mL of dry $CH_3CN$, then N,N-diisopropylethylamine (0.04 g, 0.3 mmol), HBTU (0.113 g, 0.3 mmol), and methylamine were added slowly. The reaction was stirred at 25° C. for 7 hours. It was then quenched with 5 mL of saturated $NaHCO_3$, extracted with ethyl acetate (15 mLx3). The organic layers were combined and concentrated. Finally, the crude product was purified by silica gel column (hexane/ethyl acetate=3:1 to 1:1) to yield the product with 78% yield.

MS: 332.0 (M+1 for $C_{12}H_9Cl_2N_3O_2S$), TLC: $SiO_2$, $R_f$=0.44 (1:1 hexane/EtOAc). Mp: >230° C., HPLC: C-18 Column ($H_2O/CH_3CN$=1/1 with 0.1% TFA), RT Time: 4.44 minutes, Purity: 99.4%. $^1$H NMR (400 MHz, $CDCl_3$) δ 2.63 (s, 3H), 6.89 (s, 1H), 7.17 (t, 1H, J=8.1 Hz), 7.51 (d, 2H, J=8.1 Hz), 8.68 (s, 1H), 12.86 (s, 1H).

EXAMPLE 7

[2-(2,6-Dichloro-phenylamino)-4-oxo-4H-thiazol-5-ylidene]-N-ethyl-acetamide

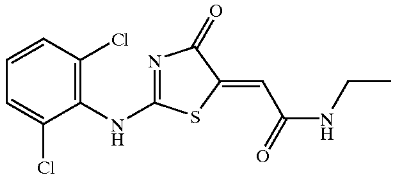

Example 7 was synthesized in accordance with the methods of Example 6, except that ethylamine was used instead of the methylamine.

MS: 343 (M+1 for $C_{13}H_{11}Cl_2N_3O_2S$), TLC: $SiO_2$, $R_f$=0.4 (1:1 hexane/EtOAc); Mp: >250° C., HPLC: C-18 Column ($H_2O/CH_3CN$=1:1 with 0.1% TFA), RT Time 2.96 minutes, Purity: 93%. 1H NMR (400 MHz, DMSO) δ 0.99 (t, 3H, J=8.3 Hz), 3.06–3.13 (m, 2H), 6.89 (s, 1H), 7.18 (t, 1H, J=8.3 Hz), 7.52 (d, 2H, J=8.1 Hz), 8.73 (m, 1H).

EXAMPLE 8

[2-(2,6-Dichloro-phenylamino)-4-oxo-4H-thiazol-5-ylidene]-N-propyl-acetamide

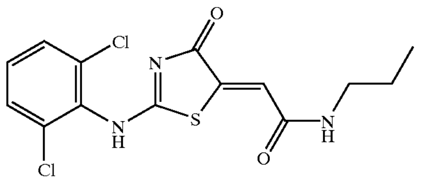

Example 8 was synthesized in accordance with the methods of Example 6, except that n-propylamine was used instead of the methylamine. It was purified by silica gel column (hexane/ethyl acetate=3:1 to 1:1) to yield the desired product (79%).

MS: 360.0 (M+1 for $C_{14}H_{13}Cl_2N_3O_2S$), TLC: $SiO_2$, $R_f$=0.68 (1:1 hexane/EtOAc). Mp: >230° C., HPLC: C-18 Column ($H_2O/CH_3CN$=1:1 with 0.1% TFA), RT Time 8.35 minutes, Purity: 98%. Analysis ($C_{14}H_{13}Cl_2N_3O_2S$): (calc) C: 46.94, H: 3.66, N: 11.73, (found) C: 47.04, H: 3.71, N: 11.38. $^1$H NMR (400 MHz, $CDCl_3$) δ 0.78 (t, 3H, J=7.4 Hz), 1.36 (m, 2H), 3.03 (q, 2H, 6.6 Hz), 6.91 (s, 1H), 7.16 (t, 1H, J=8.0 Hz), 7.49 (d, 2H, J=8.1 Hz), 8.70 (s, 1H), 12.84 (s, 1H).

EXAMPLE 9

[2-(2,6-Dichloro-phenylamino)-4-oxo-4H-thiazol-5-ylidene]-N-benzyl-acetamide

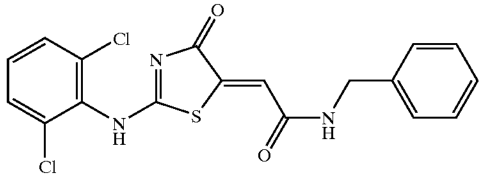

Example 9 was synthesized in accordance with the methods of Example 6, except that benzylamine was used instead of the methylamine. It was purified by silica gel column (hexane/ethyl acetate=3:1 to 1:1) to yield the desired product (81%).

MS: 408.0 (M+1 for $C_{18}H_{13}Cl_2N_3O_2$), TLC: $SiO_2$, $R_f$=0.68 (1:1 hexane/EtOAc). Mp: 204.8–205.6° C., LCMS: C-18 Column ($H_2O/CH_3CN$=1:1 with 0.1% TFA), RT Time 13.53 minutes, Purity: 98%. Analysis ($C_{18}H_{13}Cl_2N_3O_2S$): (calc) C: 53.21, H: 3.23, N: 10.34, (found) C: 53.61, H: 3.25, N: 9.01. $^1$H NMR (400 MHz, $CDCl_3$) δ 4.87 (s, 2H), 6.94 (s, 1H), 7.11 (t, 1H, J=8.3 Hz), 7.20–7.35 (m, 5H), 7.39 (d, 2H, J=8.1 Hz) 8.70 (s, 1H), 12.84 (s, 1H).

EXAMPLE 10

[2-(2,6-Dichloro-phenylamino)-4-oxo-4H-thiazol-5-ylidene]-N-methoxy-acetamide

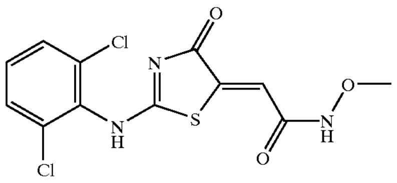

Example 10 was synthesized in accordance with the methods of Example 6, except methoxyamine was used instead of the methylamine. It was purified by silica gel column (hexane/ethyl acetate=3:1 to 1:1) to yield the desired product (71%).

MS: 348.0 (M+1 for $C_{12}H_9Cl_2N_3O_3S$), TLC: $SiO_2$, $R_f$=0.47 (1:1 hexane/EtOAc). Mp: 204.8–205.6° C., HPLC: C-18 Column ($H_2O/CH_3CN$=1:1 with 0.1% TFA), RT Time 4.46 minutes, Purity: >95%. $^1$H NMR (400 MHz, $CDCl_3$) δ 3.60 (s, 3H), 6.70 (s, 1H), 6.87 (t, 1H, J=8.0 Hz), 7.16 (d, 2H, J=8.1 Hz), 8.72 (s, 1H), 12.88 (s, 1H).

EXAMPLE 11

[2-(2,4-Dichloro-phenylamino)-4-oxo-4H-thiazol-5-ylidene]-acetic Acid Methyl Ester

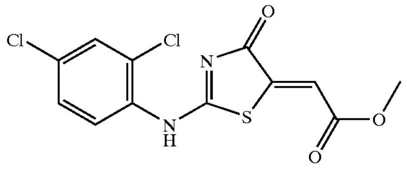

Example 11 was synthesized in accordance with the methods of Example 1, except 2,4-dichlorophenylthiourea was used instead of the 2,6-dichlorophenylthiourea. The desired product was recrystallized from ethyl acetate and hexane to yield a yellow crystal (90%).

MS: 333.0 (M+1 for $C_{12}H_8Cl_2N_2O_3S$). Mp: 211.6–212.3° C., LCMS: C-18 Column ($H_2O/CH_3CN$/0.05% TFA), Ret. Time: 10.88 min., Purity: 99.93%. Analysis ($C_{12}H_8Cl_2N_2O_3S$): (calc) C: 43.52, H: 2.43, N: 8.46, (found) C: 43.59, H: 2.13, N: 8.36. $^1$H NMR (400 MHz $CDCl_3$) δ 3.31 (s, 3H), 6.69 (s, 1H), 7.12 (d, 1H, J=7.6 Hz), 7.41 (d, 1H, J=6.1 Hz), 7.68 (s, 1H), 12.95 (s, 1H).

EXAMPLE 12

[2-(2,5-Dichloro-phenylamino)-4-oxo-4H-thiazol-5-ylidene]-acetic Acid Methyl Ester

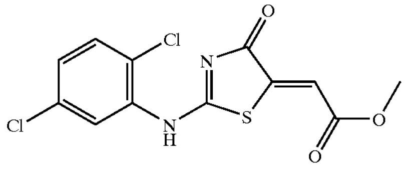

Example 12 was synthesized in accordance with the methods of Example 1, except 2,5-dichlorophenylthiourea was used instead of the 2,6-dichlorophenylthiourea. The desired product was recrystallized from ethyl acetate and hexane to yield a yellow crystal (87%).

MS: 333.0(M+1 for $C_{12}H_8Cl_2N_2O_3S$). Mp: 198.8–199.4° C., LCMS: C-18 Column ($H_2O/CH_3CN$/0.05% TFA), Ret. Time: 13.82 min., Purity: 99.89%. Analysis ($C_{12}H_8Cl_2N_2O_3S$): (calc) C: 43.52, H: 2.43, N: 8.46, (found) C: 43.60, H: 2.40, N: 8.25. $^1$H NMR (400 MHz $CDCl_3$) δ 3.31 (s, 3H), 6.72 (s, 1H), 7.24 (t, 2H, J=3.5 Hz), 7.55 (d, 1H, J=8.3 Hz), 13.01 (s, 1H).

EXAMPLE 13

[2-(2,3-Dichloro-phenylamino)-4-oxo-4H-thiazol-5-ylidene]-acetic Acid Methyl Ester

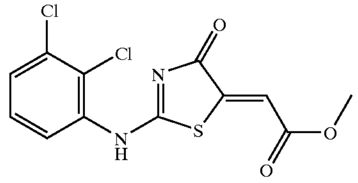

Example 13 was synthesized in accordance with the methods of Example 1, except 2,3-dichlorophenylthiourea was used instead of the 2,6-dichlorophenylthiourea. The desired product was recrystallized from ethyl acetate and hexane to yield a yellow crystal (90%).

MS: 333.0 (M+1 for $C_{12}H_8Cl_2N_2O_3S$). Mp: 204.0–204.3° C., LCMS: C-18 Column ($H_2O/CH_3CN$/0.05% TFA), Ret. Time: 10.88 min., Purity: 99.37%. Analysis ($C_{12}H_8Cl_2N_2O_3S$): (calc) C: 43.52, H: 2.43, N: 8.46, (found) C: 43.38, H: 2.51, N: 8.18. $^1$H NMR (400 MHz $CDCl_3$) δ 3.32 (s, 3H), 6.71 (s, 1H), 7.09 (d, 1H, J=7.8Hz), 7.36 (t, 1H, J=8.1 Hz), 7.44 (d, 1H, J=6.6Hz), 13.00 (s, 1H).

EXAMPLE 14

[2-(2,4,6-Trichloro-phenylamino)-4-oxo-4H-thiazol-5-ylidene]-acetic Acid Methyl Ester

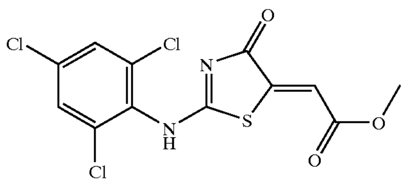

Example 13 was synthesized in accordance with the methods of Example 1, except 2,4,6-trichlorophenylthiourea was used instead of the 2,6-dichlorophenylthiourea. The desired product was recrystallized from ethyl acetate and hexane to yield a yellow crystal (91%).

MS: 366.0 (M+1 for $C_{12}H_7Cl_3N_2O_3S$). Mp: 241.3–241.7° C., LCMS: C-18 Column ($H_2O/CH_3CN$/0.05% TFA), Ret. Time: 16.04 min., Purity: 99.23%. Analysis ($C_{12}H_7Cl_3N_2O_3S$): (calc) C: 39.42, H: 1.92, N: 7.66, (found) C: 39.50, H: 2.03, N: 7.58. $^1$H NMR (400 MHz $CDCl_3$) δ 3.32 (s, 3H), 6.75 (s, 1H), 7.75 (s, 2H), 13.23 (s, 1H).

EXAMPLE 15

[2-(2-Chloro-phenylamino)-4-oxo-4H-thiazol-5-ylidene]-acetic Acid Methyl Ester

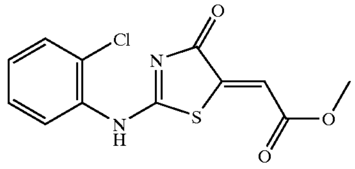

Example 15 was synthesized in accordance with the methods of Example 1, except 2-chlorophenylthiourea was used instead of the 2,6-dichlorophenylthiourea. The desired product was recrystallized from ethyl acetate and hexane to yield a yellow crystal (90%).

MS: 297.0 (M+1 for $C_{12}H_9ClN_2O_3S$). Mp: 194.0–194.6° C., LCMS: C-18 Column ($H_2O/CH_3CN$/0.05% TFA), Ret. Time: 6.48 min., Purity: 99.87%. Analysis ($C_{12}H_8Cl_2N_2O_3S$): (calc) C: 48.57, H: 3.06, N: 9.44, (found) C: 47.46, H: 2.71, N: 9.00. $^1$H NMR (400 MHz $CDCl_3$) δ 3.30 (s, 3H), 6.68 (s, 1H), 7.08 (d, 1H, J=7.5 Hz), 7.18 (t, 1H, J=7.6 Hz), 7.33 (t, 1H, J=7.4Hz), 7.49 (d, 1H, J=8.0 Hz), 12.91 (s, 1H).

EXAMPLE 16

2-[2-(2,6-Dichloro-phenylamino)-4-oxo-4H-thiazol-5-ylidene]-N-(2-methoxy-ethyl)-acetamide

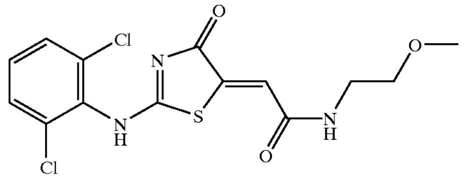

Synthesis of 2-[2-(2,6-dichloro-phenylamino)-4-oxo-4H-thiazol-5-ylidene]-N-(2-methoxy-ethyl)-acetamide. A solution of [2-(2,6-dichloro-phenylamino)-4-oxo-4H-thiazol-5-ylidene]-acetic acid (0.1 M) in DMF (0.513 mL) was treated with a solution of the 2-methoxy-ethyl amine (1.5 M) and HOBt in $CH_2Cl_2$ (0.225 mL). The reaction was placed in a Bohdan Miniblock apparatus and shaken at 50° C. for 16 hours. The reaction was cooled to room temperature, treated with polymer-supported polyamine quench resin (Aldrich, 100 mg), and shaken for 3 hours. The solution was filtered and concentrated. The residue was purified by preparative HPLC on a Phenomenex Develofil 28×100 mm C-18 column eluting with a gradient of 10% to 100% $CH_3CN/H_2O$+3% n-propanol over 6.5 minutes.

MS: 375.4 (M+1 for $C_{14}H_{13}Cl_2N_3O_3S$), HPLC (C-18 column, $H_2O+CH_3CN$+0.1% formic acid): RT: 3.3 min, purity 90%.

EXAMPLE 17

2-(2,6-Dichloro-phenylamino)-5-(2-oxo-2-piperidine-1-yl-ethylidene)-thiazol-4-one

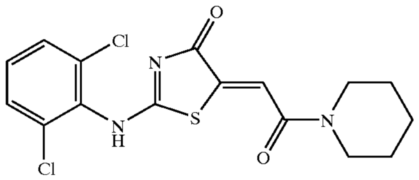

Synthesis of 2-(2,6-dichloro-phenylamino)-5-(2-oxo-2-piperidine-1-yl-ethylidene)-thiazol-4-one: Example 17 was synthesized in accordance with the methods of Example 16 except that piperidine was used instead of 2-methoxy-ethyl amine.

MS: 385.3 (M+1 for $C_{16}H_{15}Cl_2N_3O_2S$), HPLC (C-18 column, $H_2O+CH_3CN+0.1\%$ formic acid): RT: 3.7 min, purity 100%.

EXAMPLE 18

2-(2,6-Dichloro-phenylamino)-5-[2-(4-ethyl-piperazin-1-yl)-2-oxo-ethylidene)-thiazol-4-one

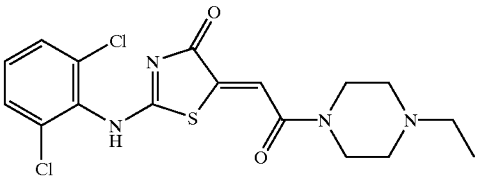

Synthesis of 2-(2,6-dichloro-phenylamino)-5-[2-(4-ethyl-piperazin-1-yl)-2-oxo-ethylidene)-thiazol-4-one: Example 18 was synthesized in accordance with the methods of Example 16 except that N-ethylpiperazine was used instead of 2-methoxy-ethyl amine.

MS: 414.3 (M+1 for $C_{17}H_{18}Cl_2N_4O_2S$), HPLC (C-18 column, $H_2O+CH_3CN+0.1\%$ formic acid): RT: 2.7 min, purity 92%.

EXAMPLE 19

2-[2-(2,6-Dichloro-phenylamino)-4-oxo-4H-thiazol-5-ylidene]-N-(3-pyrrolidin-1-yl-propyl)-acetamide

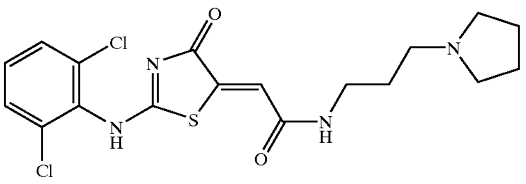

Synthesis of 2-[2-(2,6-dichloro-phenylamino)-4-oxo-4H-thiazol-5-ylidene]-N-(3-pyrrolidin-1-yl-propyl)-acetamide: Example 19 was synthesized in accordance with the methods of Example 16 except that 3-pyrrolidinopropylamine was used instead of 2-methoxy-ethyl amine.

MS: 428.4 (M+1 for $C_{18}H_{20}Cl_2N_4O_2S$), HPLC (C-18 column, $H_2O+CH_3CN+0.1\%$ formic acid): RT: 2.5 min, purity 76%.

EXAMPLE 20

2-[2-(2,6-Dichloro-phenylamino)-4-oxo-4H-thiazol-5-ylidene]-N-isopropyl-acetamide

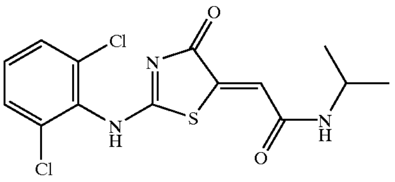

Synthesis of 2-[2-(2,6-dichloro-phenylamino)-4-oxo-4H-thiazol-5-ylidene]-N-isopropyl-acetamide: Example 20 was synthesized in accordance with the methods of Example 16 except that isopropyl amine was used instead of 2-methoxy-ethyl amine.

MS: 359.3 (M+1 for $C_{14}H_{13}Cl_2N_3O_2S$), HPLC (C-18 column, $H_2O+CH_3CN+0.1\%$ formic acid): RT: 3.5 min, purity 96%.

EXAMPLE 21

2-(2,6-Dichloro-phenylamino)-5-(2-oxo-2-pyrrolidin-1-yl-ethylidene)-thiazol-4-one

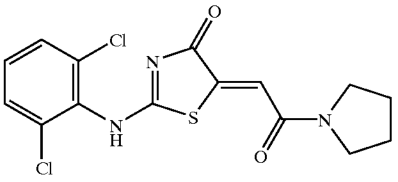

Synthesis of 2-(2,6-dichloro-phenylamino)-5-(2-oxo-2-pyrrolidin-1-yl-ethylidene)-thiazol-4-one: Example 21 was synthesized in accordance with the methods of Example 16 except that pyrrolidine was used instead of 2-methoxy-ethyl amine.

MS: 371.3 (M+1 for $C_{15}H_{13}Cl_2N_3O_2S$), HPLC (C-18 column, $H_2O+CH_3CN+0.1\%$ formic acid): RT: 3.4 min, purity 96%.

EXAMPLE 22

N-Cyclohexyl-2-[2-(2,6-dichloro-phenylamino)-4-oxo-4H-thiazol-5-ylidene]-acetamide

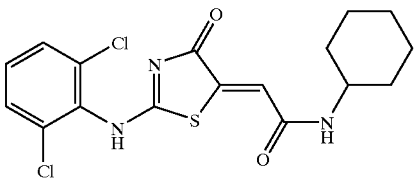

Synthesis of N-cyclohexyl-2-[2-(2,6-dichloro-phenylamino)-4-oxo-4H-thiazol-5-ylidene]-acetamide: Example 22 was synthesized in accordance with the methods of Example 16 except that cyclohexyl amine was used instead of 2-methoxy-ethyl amine.

EXAMPLE 23

2-[2-(2,6-Dichloro-phenylamino)-4-oxo-4H-thiazol-5-ylidene]-N-(2,2-dimethoxy-ethyl)-acetamide

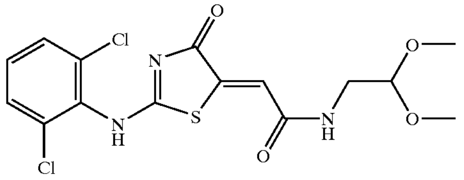

Synthesis of 2-[2-(2,6-dichloro-phenylamino)-4-oxo-4H-thiazol-5-ylidene]-N-(2,2-dimethoxy-ethyl)-acetamide: Example 23 was synthesized in accordance with the methods of Example 16 except that aminoacetaldehyde dimethyl acetal was used instead of 2-methoxy-ethyl amine.

MS: 405.3 (M+1 for $C_{15}H_{15}Cl_2N_3O_4S$), HPLC (C-18 column, $H_2O+CH_3CN+0.1\%$ formic acid): RT: 3.3 min, purity 100%.

EXAMPLE 24

2-(2,6-Dichloro-phenylamino)-5-[2-(3,5-dimethyl-piperidin-1-yl)-2-oxo-ethylidene)-thiazol-4-one

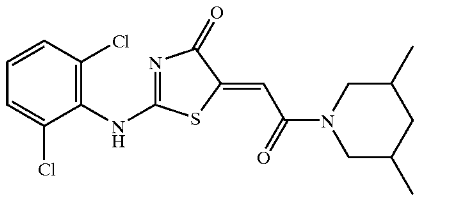

Synthesis of 2-(2,6-dichloro-phenylamino)-5-[2-(3,5-dimethyl-piperidin-1-yl)-2-oxo-ethylidene)-thiazol-4-one: Example 24 was synthesized in accordance with the methods of Example 16 except that 3,5-dimethyl piperidine was used instead of 2-methoxy-ethyl amine.

MS: 413.3 (M+1 for $C_{18}H_{19}Cl_2N_3O_2S$), HPLC (C-18 column, $H_2O+CH_3CN+0.1\%$ formic acid): RT: 4.1 min, purity 85%.

EXAMPLE 25

2-(2,6-Dichloro-phenylamino)-5-[2-(3-dimethylamino-pyrrolidin-1-yl)-2-oxo-ethylidene)-thiazol-4-one

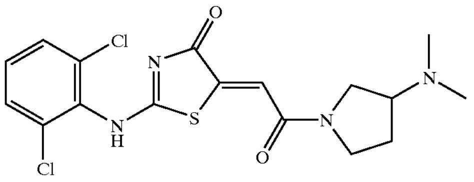

Synthesis of 2-(2,6-dichloro-phenylamino)-5-[2-(3-dimethylamino-pyrrolidin-1-yl)-2-oxo-ethylidene)-thiazol-4-one: Example 25 was synthesized in accordance with the methods of Example 16 except that 3-dimethylamino pyrrolidine was used instead of 2-methoxy-ethyl amine.

MS: 414.3 (M+1 for $C_{17}H_{18}Cl_2N_4O_2S$), HPLC (C-18 column, $H_2O+CH_3CN+0.1\%$ formic acid): RT: 2.4 min, purity 97%.

EXAMPLE 26

2-[2-(2,6-Dichloro-phenylamino)-4-oxo-4H-thiazol-5-ylidene]-N-[2-(2-hydroxy-ethoxy)-ethyl]-acetamide

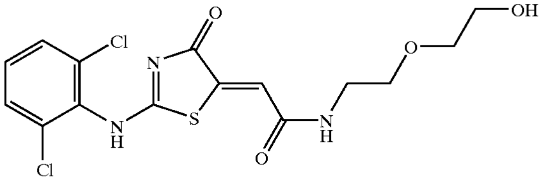

Synthesis of 2-[2-(2,6-dichloro-phenylamino)-4-oxo-4H-thiazol-5-ylidene]-N-[2-(2-hydroxy-ethoxy)-ethyl]-acetamide: Example 26 was synthesized in accordance with the methods of Example 16 except that 2-(2-aminoethoxy) ethanol was used instead of 2-methoxy-ethyl amine.

MS: 405.3 (M+1 for $C_{15}H_{15}Cl_2N_3O_4S$), HPLC (C-18 column, $H_2O+CH_3CN+0.1\%$ formic acid): RT: 4 min, purity 99%.

EXAMPLE 27

2-[2-(2,6-Dichloro-phenylamino)-4-oxo-4H-thiazol-5-ylidene]-N-(3-methylsulfanyl-propyl)-acetamide

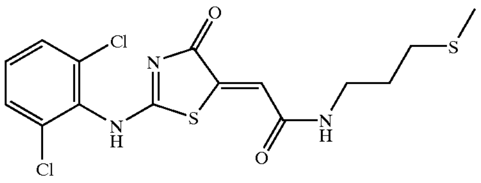

Synthesis of 2-[2-(2,6-dichloro-phenylamino)-4-oxo-4H-thiazol-5-ylidene]-N-(3-methylsulfanyl-propyl)-acetamide: Example 27 was synthesized in accordance with the methods of Example 16 except that 3-(methylthio)propyl amine was used instead of 2-methoxy-ethyl amine.

MS: 405.3 (M+1 for $C_{15}H_{15}Cl_2N_3O_2S_2$), HPLC (C-18 column, $H_2O+CH_3CN+0.1\%$ formic acid): RT: 3.5 min, purity 93%.

EXAMPLE 28

2-[2-(2,6-Dichloro-phenylamino)-4-oxo-4H-thiazol-5-ylidene]-N-(2,3-dihydroxy-propyl)-acetamide

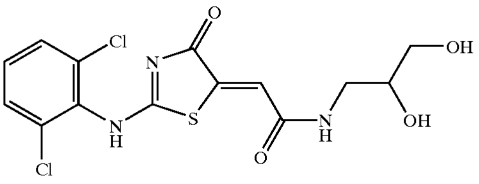

Synthesis of 2-[2-(2,6-dichloro-phenylamino)-4-oxo-4H-thiazol-5-ylidene]-N-(2,3-dihydroxy-propyl)-acetamide: Example 28 was synthesized in accordance with the methods of Example 16 except that 2,3-dihydroxypropyl amine was used instead of 2-methoxy-ethyl amine.

MS: 391.3 (M+1 for $C_{14}H_{13}Cl_2N_3O_4S$), HPLC (C-18 column, $H_2O$+$CH_3CN$+0.1% formic acid): RT: 2.7 min, purity 97%.

EXAMPLE 29

2-[2-(2,6-Dichloro-phenylamino)-4-oxo-4H-thiazol-5-ylidene]-N-(2-methyl-allyl)-acetamide

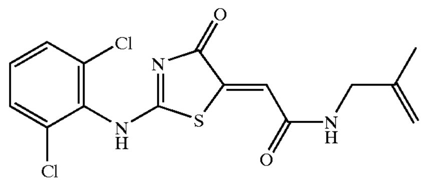

Synthesis of 2-[2-(2,6-dichloro-phenylamino)-4-oxo-4H-thiazol-5-ylidene]-N-(2-methyl-allyl)-acetamide: Example 29 was synthesized in accordance with the methods of Example 16 except that methallyl amine was used instead of 2-methoxy-ethyl amine.

MS: 371.3 (M+1 for $C_{15}H_{13}Cl_2N_3O_2S$), HPLC (C-18 column, $H_2O$+$CH_3CN$+0.1% formic acid): RT: 3.6 min, purity 100%.

EXAMPLE 30

N-Cyclopentyl-2-[2-(2,6-dichloro-phenylamino)-4-oxo-4H-thiazol-5-ylidene]-acetamide

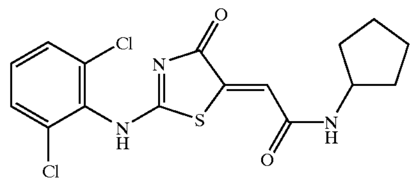

Synthesis of N-cyclopentyl-2-[2-(2,6-dichloro-phenylamino)-4-oxo-4H-thiazol-5-ylidene]-acetamide: Example 30 was synthesized in accordance with the methods of Example 16 except that cyclopentyl amine was used instead of 2-methoxy-ethyl amine.

MS: 385.3 (M+1 for $C_{16}H_{15}Cl_2N_3O_2S$), HPLC (C-18 column, $H_2O$+$CH_3CN$+0.1% formic acid): RT: 3.8 min, purity 99%.

EXAMPLE 31

N-Cyclopropylmethyl-2-[2-(2,6-dichloro-phenylamino)-4-oxo-4H-thiazol-5-ylidene]-N-propyl-acetamide

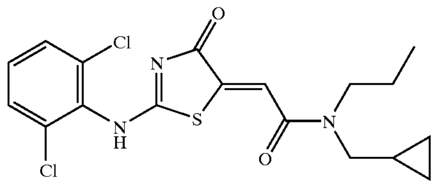

Synthesis of N-cyclopropyl methyl-2-[2-(2,6-dichloro-phenylamino)-4-oxo-4H-thiazol-5-ylidene]-N-propyl-acetamide: Example 31 was synthesized in accordance with the methods of Example 16 except that N-propylcyclopropanemethyl amine was used instead of 2-methoxy-ethyl amine.

MS: 413.3 (M+1 for $C_{18}H_{19}Cl_2N_3O_2S$), HPLC (C-18 column, $H_2O$+$CH_3CN$+0.1% formic acid): RT: 4.0 min, purity 95%.

EXAMPLE 32

2-[2-(2,6-Dichloro-phenylamino)-4-oxo-4H-thiazol-5-ylidene]-N-methyl-N-(1-methyl-pyrrolidin-3-yl)-acetamide

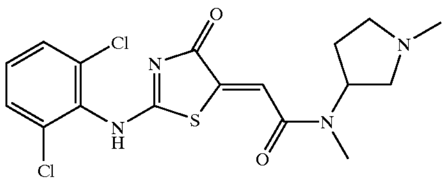

Synthesis of 2-[2-(2,6-dichloro-phenylamino)-4-oxo-4H-thiazol-5-ylidene]-N-methyl-N-(1-methyl-pyrrolidin-3-yl)-acetamide: Example 32 was synthesized in accordance with the methods of Example 16 except that N,N'-dimethyl-3-aminopyrrolidine was used instead of 2-methoxy-ethyl amine.

MS: 414.3 (M+1 for $C_{17}H_{18}Cl_2N_4O_2S$), HPLC (C-18 column, $H_2O$+$CH_3CN$+0.1% formic acid): RT: 2.6 min, purity 99%.

EXAMPLE 33

2-[2-(2,6-Dichloro-phenylamino)-4-oxo-4H-thiazol-5-ylidene]-N-(2-phenoxy-ethyl)-acetamide

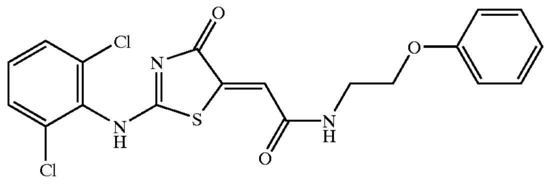

Synthesis of 2-[2-(2,6-dichloro-phenylamino)-4-oxo-4H-thiazol-5-ylidene]-N-(2-phenoxy-ethyl)-acetamide: Example 33 was synthesized in accordance with the methods of Example 16 except that 2-phenoxy ethyl amine was used instead of 2-methoxy-ethyl amine.

MS: 437.3 (M+1 for $C_{19}H_{15}Cl_2N_3O_3S$), HPLC (C-18 column, $H_2O$+$CH_3CN$+0.1% formic acid): RT: 3.8 min, purity 84%.

EXAMPLE 34

2-[2-(2,6-Dichloro-phenylamino)-4-oxo-4H-thiazol-5-ylidene]-N-methyl-N-(8-methylamino-octyl)-acetamide

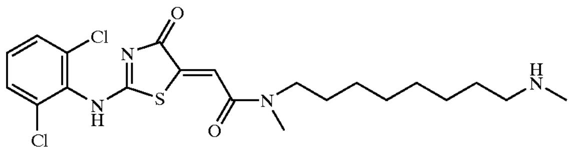

Synthesis of 2-[2-(2,6-dichloro-phenylamino)-4-oxo-4H-thiazol-5-ylidene]-N-methyl-N-(8-methylamino-octyl)-acetamide: Example 34 was synthesized in accordance with the methods of Example 16 except that N,N'-dimethyl-1,8-octanediamine was used instead of 2-methoxy-ethyl amine.

MS: 472.5 (M+1 for $C_{21}H_{28}Cl_2N_4O_2S$), HPLC (C-18 column, $H_2O$+$CH_3CN$+0.1% formic acid): RT: 2.7 min, purity 93%.

EXAMPLE 35

N-(4-Chloro-benzyl)-2-[2-(2,6-dichloro-phenylamino)-4-oxo-4H-thiazol-5-ylidene]-acetamide

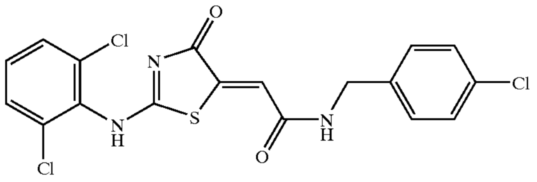

Synthesis of N-(4-chloro-benzyl)-2-[2-(2,6-dichloro-phenylamino)-4-oxo-4H-thiazol-5-ylidene]-acetamide: Example 35 was synthesized in accordance with the methods of Example 16 except that 4-chlorobenzyl amine was used instead of 2-methoxy-ethyl amine.

MS: 441.7 (M+1 for $C_{18}H_{12}Cl_3N_3O_2S$).

EXAMPLE 36

N-(1-Benzyl-pyrrolidin-3-yl)-2-[2-(2,6-dichloro-phenylamino)-4-oxo-4H-thiazol-5-ylidene]-N-methyl-acetamide

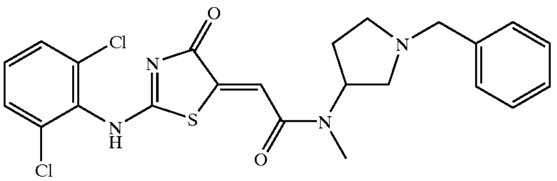

Synthesis of N-(1-benzyl-pyrrolidin-3-yl)-2-[2-(2,6-dichloro-phenylamino)-4-oxo-4H-thiazol-5-ylidene]-N-methyl-acetamide: Example 36 was synthesized in accordance with the methods of Example 16 except that 1-benzyl-3-(methylamino)pyrrolidine was used instead of 2-methoxy-ethyl amine.

MS: 490.4 (M+1 for $C_{23}H_{22}Cl_2N_4O_2S$).

EXAMPLE 37

2-[2-(2,6-Dichloro-phenylamino)-4-oxo-4H-thiazol-5-ylidene]-N-(1,4-dimethyl-pentyl)-acetamide

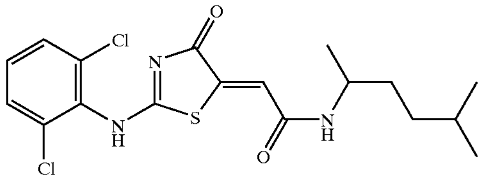

Synthesis of 2-[2-(2,6-dichloro-phenylamino)-4-oxo-4H-thiazol-5-ylidene]-N-(1,4-dimethyl-pentyl)-acetamide: Example 37 was synthesized in accordance with the methods of Example 16 except that 1,4-dimethylpentyl amine was used instead of 2-methoxy-ethyl amine.

MS: 415.4 (M+1 for $C_{18}H_{21}Cl_2N_3O_2S$).

EXAMPLE 38

2-[2-(2,6-Dichloro-phenylamino)-4-oxo-4H-thiazol-5-ylidene]-N-(1 ,3-dimethyl-butyl)-acetamide

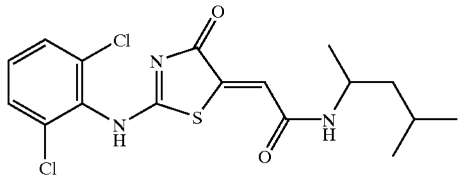

Synthesis of 2-[2-(2,6-dichloro-phenylamino)-4-oxo-4H-thiazol-5-ylidene]-N-(1,3-dimethyl-butyl)-acetamide: Example 38 was synthesized in accordance with the methods of Example 16 except that 1,3-dimethylbutyl amine was used instead of 2-methoxy-ethyl amine.

MS: 401.3 (M+1 for $C_{17}H_{19}Cl_2N_3O_2S$).

EXAMPLE 39

N-Cycloheptyl-2-[2-(2,6-dichloro-phenylamino)-4-oxo-4H-thiazol-5-ylidene]-acetamide

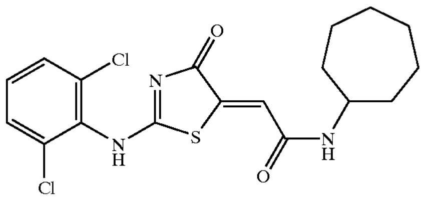

Synthesis of N-cycloheptyl-2-[2-(2,6-dichloro-phenylamino)-4-oxo-4H-thiazol-5-ylidene]-acetamide: Example 39 was synthesized in accordance with the methods of Example 16 except that cycloheptyl amine was used instead of 2-methoxy-ethyl amine.

MS: 413.4 (M+1 for $C_{18}H_{19}Cl_2N_3O_2S$).

In vitro enzyme assay—human Branched Chain Amino Acid Aminotransferase cytosolic form (hBCATc) and mitochondrial form (hBCATm) were assayed at 37° C. in 25 mM phosphate buffer pH 7.8. In addition, 2 mM DTT and 12.5 mM EDTA were added to the assay mixture. A coupling enzyme assay was used to monitor the production of glutamate. The formation of NADH from NAD+at 340 nM was followed on a 96-well plate Molecular Devices plate reader. The following components were used in this coupled assay: 4 mM ADP, 1 mM NAD+, 750 μM L-Leucine, 500 μM (α-ketoglutarate, 10 μM pyridoxal phosphate, 1 unit glutamate dehydrogenase, and 1.25 μg of the appropriate BCAT enzyme. Inhibitions by compounds were assayed by adding various concentrations to this coupled assay procedure as a DMSO stock up to a 5% v/v DMSO/buffer ratio. Data is shown in Table 1.

Enzyme Preparation—humanBCATc was expressed in BL21(DE3) cells. A growing culture of cells was induced with 1 mM IPTG at room temperature overnight. These cells were harvested by centrifugation at 10,000 g for 20 minutes. The supernatant was discarded, and the cells were stored at −80° C. until needed. The protein was purified by the following method. The cell paste was resuspended in extraction buffer (0.1 M phosphate, pH 8.0, with 0.01 M Tris-HCL and 5 mM TCEP and then lysed on a French Press at 1000 psi. The lysate was centrifuged at 10,000 g for 15 minutes, and the pellet was discarded. The supernatant was loaded onto a Hitrap Chelating column previously charged with 0.1 M $NiSO_4$ and washed with 3 to 4 column volumes of extraction buffer. The column was then washed with 0.01 Tris, pH 7.5, 10% glycerol, 150 mM NaCl, 5 mM TCEP for two column volumes. The column was then further washed with two column volumes of 0.1 M phosphate, pH 6.0, 0.01 M Tris, 10% glycerol and 750 mM NaCl. Finally, the column was washed with two column volumes of the same buffer plus 50 mM imidazole. The BCAT enzyme was then eluted with the same buffer but with 350 mM imidazole. The eluant was then dialyzed overnight against 10 mM phosphate buffer pH 8.0, 10% glycerol, and 5 mM TCEP. The dialyzed protein was then loaded onto a Q-sepharose column and eluted using a salt gradient. Active fractions were collected and further purified on a Superose-12 column to yield pure BCAT protein.

TABLE 1

| Example Number | Structure | hBCATc $I_{50}$ (μM) |
|---|---|---|
| 1 | 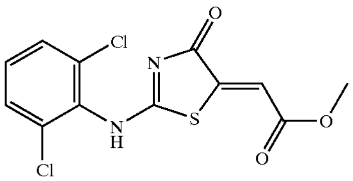 | 4.1 |
| 2 | 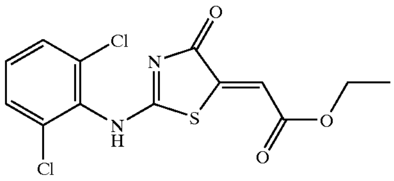 | 52.5 |
| 3 | 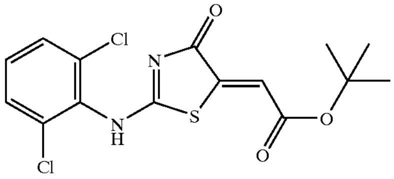 | 68.6, 36.9 |
| 4 | 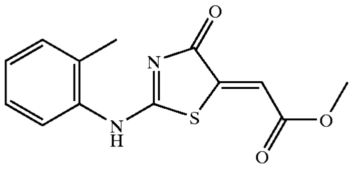 | 43.9, 29.6 |
| 5 | 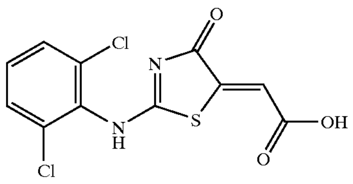 | 18.6, 13.1 |

TABLE 1-continued
| Example Number | Structure | hBCATc $I_{50}$ ($\mu$M) |
|---|---|---|
| 6 | 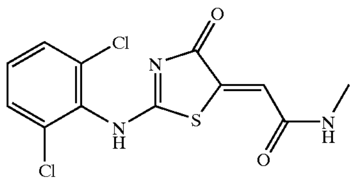 | 3.1, 1.9 |
| 7 | 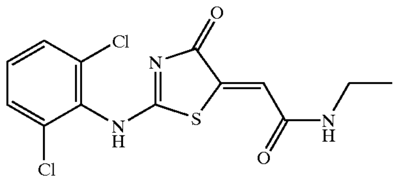 | 13.1, 3.15 |
| 8 | 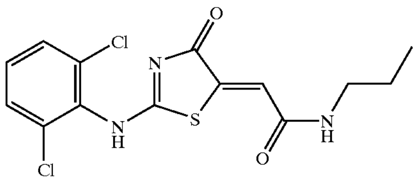 | 35.7, 17.4 |
| 9 | 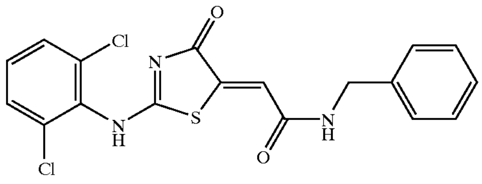 | 33, 24.0 |
| 10 | 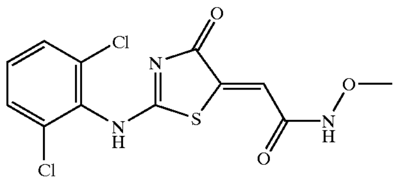 | 31.7 |
| 11 | 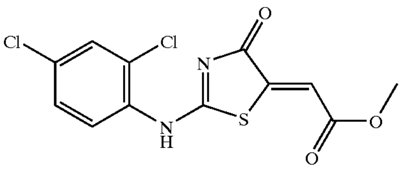 | 30.1 |
| 12 | 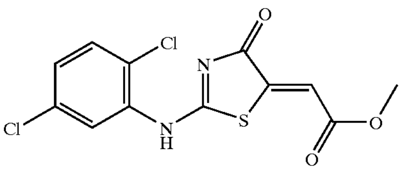 | 27.6 |
| 13 | 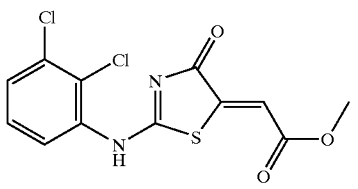 | 18.7 |

TABLE 1-continued
| Example Number | Structure | hBCATc $I_{50}$ ($\mu$M) |
|---|---|---|
| 14 | 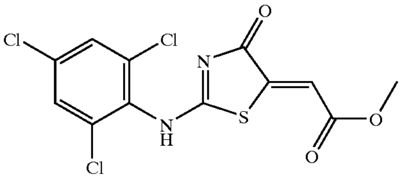 | 16.6 |
| 15 | 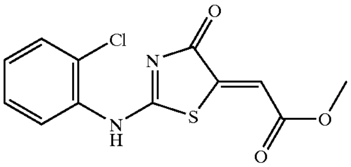 | 19.5 |
| 16 | 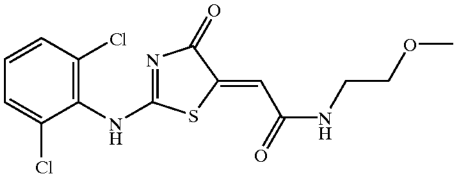 | 82.7 |
| 17 | 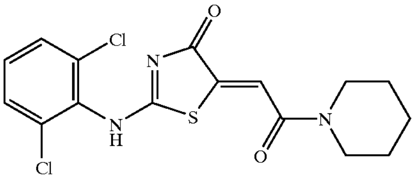 | 12.8 |
| 18 | 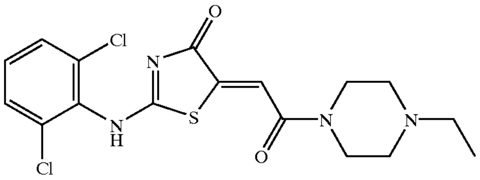 | 64.1 |
| 19 | 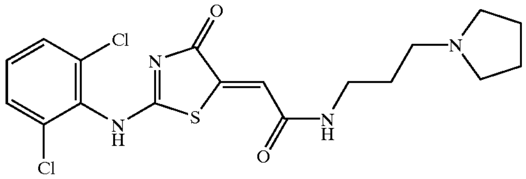 | 55.0 |
| 20 | 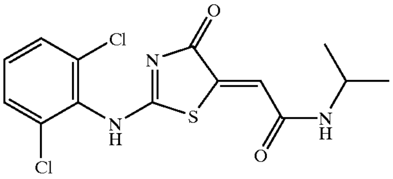 | 65.9 |
| 21 | 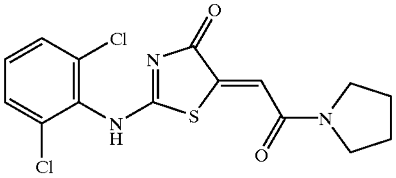 | 13.8 |

TABLE 1-continued
| Example Number | Structure | hBCATc $I_{50}$ (μM) |
|---|---|---|
| 22 | 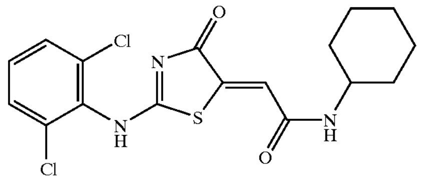 | 22.6 |
| 23 | 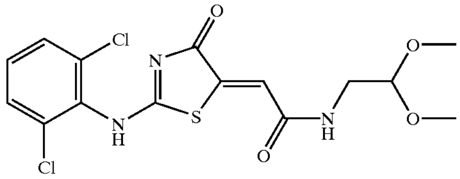 | 39.8 |
| 24 | 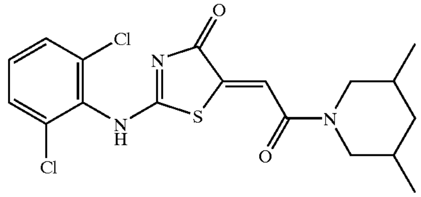 | 8.97 |
| 25 | 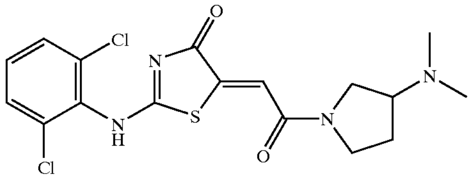 | 65.1 |
| 26 | 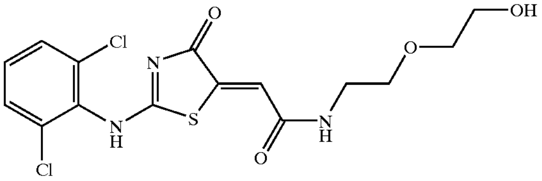 | 56.3 |
| 27 | 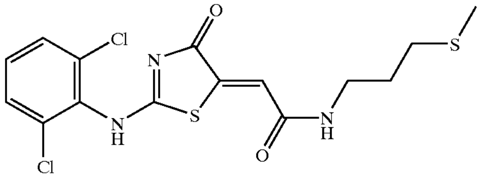 | 41.2 |
| 28 | 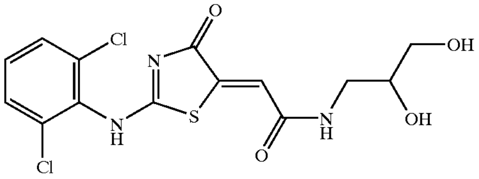 | 66.9 |
| 29 | 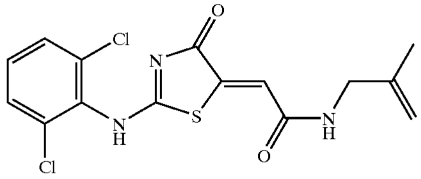 | 31.1 |

TABLE 1-continued
| Example Number | Structure | hBCATc $I_{50}$ ($\mu$M) |
|---|---|---|
| 30 | 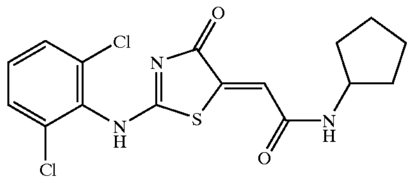 | 16.6 |
| 31 | 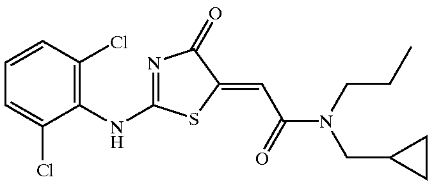 | 11.2 |
| 32 | 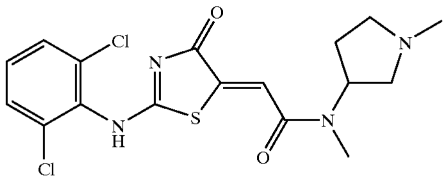 | 89.8 |
| 33 | 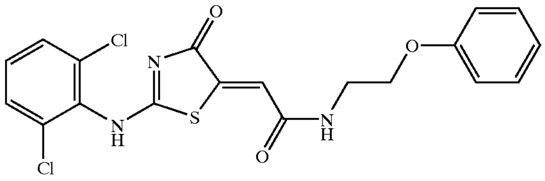 | 40.4 |
| 34 | 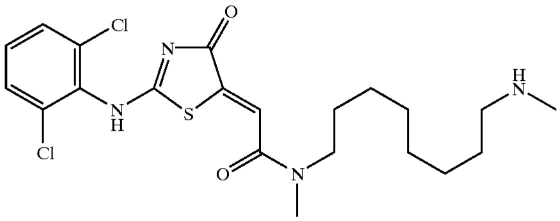 | 75.6 |
| 35 | 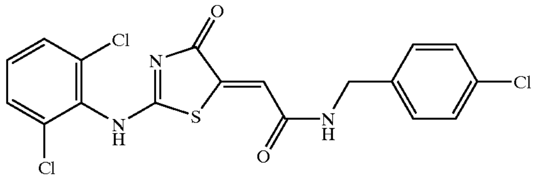 | Inhibit 130% @ 20 $\mu$M |
| 36 | 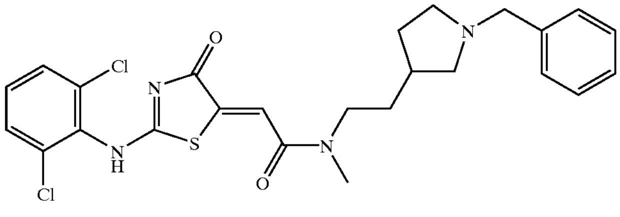 | Inhibit 29% @ 20 $\mu$M |

TABLE 1-continued

| Example Number | Structure | hBCATc $I_{50}$ (μM) |
|---|---|---|
| 37 | 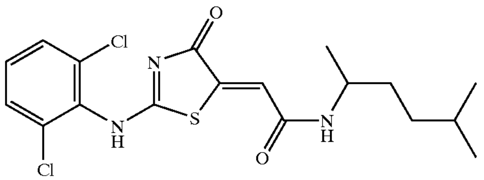 | Inhibit 34% @ 20 μM |
| 38 | 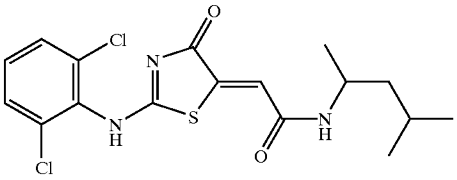 | Inhibit 33% @ 20 μM |
| 39 | 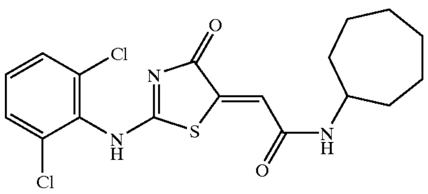 | Inhibit 39% @ 20 μM |

What is claimed is:

1. A compound of Formula I

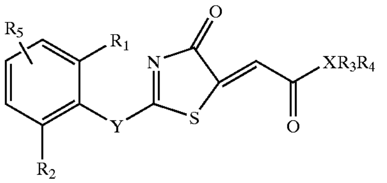

I wherein:

X is N or O;

Y is NH or $CH_2$;

$R_1$ and $R_2$ are independently hydrogen, halogen, or $C_1$–$C_3$ alkyl, with the proviso that both $R_1$ and $R_2$ cannot be hydrogen at the same time;

when X is N then $R_3$ and $R_4$ are independently hydrogen, alkyl, substituted alkyl, cycloalkyl, substituted cycloalkyl, alkenyl, substituted alkenyl, heterocyclyl, substituted heterocyclyl, arylalkyl, substituted arylalkyl, alkoxy, substituted alkoxy, arylalkoxy, or substituted arylalkoxy; or $R_3$ and $R_4$ together with X constitute a substituted or unsubstituted heterocyclyl group;

when X is O then $R_3$ is hydrogen, alkyl, substituted alkyl, cycloalkyl, substituted cycloalkyl, alkenyl, substituted alkenyl, heterocyclyl, substituted heterocyclyl, arylalkyl, substituted arylalkyl, alkoxy, substituted alkoxy, arylalkoxy, or substituted arylalkoxy and $R_4$ is absent; and $R_5$ is hydrogen or halogen;

or a pharmaceutically acceptable salt, ester, prodrug, or amide thereof.

2. A compound according to claim 1 wherein $R_5$ is hydrogen.

3. A compound according to claim 1 wherein $R_1$ is Cl.

4. A compound according to claim 1 wherein $R_1$ and $R_2$ are Cl.

5. A compound according to claim 1 wherein X is O.

6. A compound according to claim 5 wherein $R_3$ is alkyl.

7. A compound according to claim 1 wherein X is N.

8. A compound according to claim 1 wherein $R_3$ is alkyl or cycloalkyl and $R_4$ is hydrogen or alkyl, or $R_3$ and $R_4$ together with X constitute a pyrrolidine, piperidine, morpholine or N-alkylpiperazine ring.

9. A compound according to claim 8 wherein $R_3$ is alkyl and $R_4$ is hydrogen.

10. A compound according to claim 1 selected from:

[2-(2,6-Dichloro-phenylamino)-4-oxo-4H-thiazol-5-ylidene]-acetic acid methyl ester;

[2-(2,6-Dichloro-phenylamino)-4-oxo-4H-thiazol-5-ylidene]-acetic acid ethyl ester;

[2-(2,6-Dichloro-phenylamino)-4-oxo-4H-thiazol-5-ylidene]-acetic acid tert-butyl ester;

[2-(2-Methyl-phenylamino)-4-oxo-4H-thiazol-5-ylidene]-acetic acid methyl ester;

[2-(2,6-Dichloro-phenylamino)-4-oxo-4H-thiazol-5-ylidene]-acetic acid;

[2-(2,6-Dichloro-phenylamino)-4-oxo-4H-thiazol-5-ylidene]-N-methyl-acetamide;

[2-(2,6-Dichloro-phenylamino)-4-oxo-4H-thiazol-5-ylidene]-N-ethyl-acetamide;

[2-(2,6-Dichloro-phenylamino)-4-oxo-4H-thiazol-5-ylidene]-N-propyl-acetamide; [2-(2,6-Dichloro-phenylamino)-4-oxo-4H-thiazol-5-ylidene]-N-benzyl-acetamide;

[2-(2,6-Dichloro-phenylamino)-4-oxo-4H-thiazol-5-ylidene]-N-methoxy-acetamide;

[2-(2,4-Dichloro-phenylamino)-4-oxo-4H-thiazol-5-ylidene]-acetic acid methyl ester;

[2-(2,5-Dichloro-phenylamino)-4-oxo-4H-thiazol-5-ylidene]-acetic acid methyl ester;

[2-(2,3-Dichloro-phenylamino)-4-oxo-4H-thiazol-5-ylidene]-acetic acid methyl ester;

[2-(2,4,6-Trichloro-phenylamino)-4-oxo-4H-thiazol-5-ylidene]-acetic acid methyl ester;

[2-(2-Chloro-phenylamino)-4-oxo-4H-thiazol-5-ylidenel-acetic acid methyl ester;

2-(2,6-Dichloro-phenylamino)-4-oxo-4H-thiazol-5-ylidene]-N-(2-methoxy-ethyl)-acetamide;

2,6-Dichloro-phenylamino)-5-(2-oxo-2-piperidine-1-yl-ethylidene)-thiazol-4-one;

2,6-Dichloro-phenylamino)-5-[2-(4-ethyl-piperazin-1-yl)-2-oxo-ethylidene)-thiazol-4-one;

2-(2,6-Dichloro-phenylamino)-4-oxo-4H-thiazol-5-ylidenel-N-(3-pyrrolidin-1-yl-propyl)-acetamide;

2-(2,6-Dichloro-phenylamino)-4-oxo-4H-thiazol-5-ylidene]-N-isopropyl-acetamide;

2-(2,6-Dichloro-phenylamino)-5-(2-oxo-2-pyrrolidin-1-yl-ethylidene)-thiazol-4-one;

N-Cyclohexyl-2-[2-(2,6-dichloro-phenylamino)-4-oxo-4H-thiazol-5-ylidene]-acetamide;

2-(2,6-Dichloro-phenylamino)-4-oxo-4H-thiazol-5-ylidenel-N-(2,2-dimethoxy-ethyl)-acetamide;

2-(2,6-Dichloro-phenylamino)-5-[2-(3,5-dimethyl-piperidin-1-yl)-2-oxo-ethylidene)-thiazol-4-one;

2-(2,6-Dichloro-phenylamino)-5-[2-(3-dimethylamino-pyrrolidin-1-yl)-2-oxo-ethylidene)-thiazol-4-one;

2-[2-(2,6-Dichloro-phenylamino)-4-oxo-4H-thiazol-5-ylidenel-N-[2-(2-hydroxy-ethoxy)-ethyl]-acetamide;

2-[2-(2,6-Dichloro-phenylamino)-4-oxo-4H-thiazol-5-ylidene]-N-(3-methylsulfanyl-propyl)-acetamide;

2-[2-(2,6-Dichloro-phenylamino)-4-oxo-4H-thiazol-5-ylidene]-N-(2,3-dihydroxy-propyl)-acetamide;

2-[2-(2,6-Dichloro-phenylamino)-4-oxo-4H-thiazol-5-ylidene]-N-(2-methyl-allyl)-acetamide;

N-Cyclopentyl-2-[2-(2,6-dichloro-phenylamino)-4-oxo-4H-thiazol-5-ylidene]-acetamide;

N-Cyclopropylmethyl-2-[2-(2,6-dichloro-phenyl amino)-4-oxo-4H-thiazol-5-ylidene]-N-propyl-acetamide;

2-[2-(2,6-Dichloro-phenylamino)-4-oxo-4H-thiazol-5-ylidene]-N-methyl-N-(1-methyl-pyrrolidin-3-yl)-acetamide;

2-[2-(2,6-Dichloro-phenylamino)-4-oxo-4H-thiazol-5-ylidene]-N-(2-phenoxy-ethyl)-acetamide;

2-[2-(2,6-Dichloro-phenylamino)-4-oxo-4H-thiazol-5-ylidene]-N-methyl-N-(8-methylamino-octyl)-acetamide;

N-(4-Chloro-benzyl )-2-[2-(2,6-dichloro-phenylamino)-4-oxo-4H-thiazol-5-ylidene]-acetamide;

N-(1-Benzyl-pyrrolidin-3-yl)-2-[2-(2,6-dichloro-phenylamino)-4-oxo-4H-thiazol-5-ylidene]-N-methyl-acetamide;

2-[2-(2,6-Dichloro-phenylamino)-4-oxo-4H-thiazol-5-ylidene]-N-(1,4-dimethyl-pentyl)-acetamide;

2-[2-(2,6-Dichloro-phenylamino)-4-oxo-4H-thiazol-5-ylidene]-N-(1,3-dimethyl-butyl)-acetamide; and N-Cycloheptyl-2-[2-(2,6-dichloro-phenylamino)-4-oxo-4H-thiazol-5-ylidene]-acetamide.

11. A pharmaceutical composition comprising a compound of claim 1 and a pharmaceutically acceptable carrier.

12. A method of treating or preventing neuronal loss associated with stroke, ischemia, CNS trauma, hypoglycemia or surgery, or treating a neurodegenerative disease, or treating or preventing the adverse consequences of the overstimulation of the excitatory amino acids, or treating anxiety, psychosis, glaucoma, CMV retinitis, diabetic retinopathy, urinary incontinence, migraine headache, convulsions, aminoglycoside antibiotics-induced hearing loss, Parkinson's disease, chronic pain, neuropathic pain, or inducing anesthesia, opioid tolerance or withdrawal, or enhancing cognition, comprising administering to a patient in need of such treatment an effective amount of a compound of claim 1.

13. The method of claim 12 wherein the compound is:

[2-(2,6-Dichloro-phenylamino)-4-oxo-4H-thiazol-5-ylidene]-acetic acid methyl ester;

[2-(2,6-Dichloro-phenylamino)-4-oxo-4H-thiazol-5-ylidene]-acetic acid ethyl ester;

[2-(2,6-Dichloro-phenylamino)-4-oxo-4H-thiazol-5-ylidene]-acetic acid tert-butyl ester;

[2-(2-Methyl-phenylamino)-4-oxo-4H-thiazol-5-ylidene]-acetic acid methyl ester;

[2-(2,6-Dichloro-phenylamino)-4-oxo-4H-thiazol-5-ylidene]-acetic acid;

[2-(2,6-Dichloro-phenylamino)-4-oxo-4H-thiazol-5-ylidene]-N-methyl-acetamide;

[2-(2,6-Dichloro-phenylamino)-4-oxo-4H-thiazol-5-ylidene]-N-ethyl-acetamide;

(2-(2,6-Dichloro-phenylamino)-4oxo-4H-thiazol-5-ylidene]-N-propyl-acetamide;

[2-(2,6-Dichloro-phenylamino)-4-oxo-4H-thiazol-5-ylidene]-N-benzyl-acetamide;

[2-(2,6-Dichloro-phenylamino)-4-oxo-4H-thiazol-5-ylidene]-N-methoxy-acetamide;

[2-(2,4-Dichloro-phenyl amino)-4-oxo-4H-thiazol-5-ylidene]-acetic acid methyl ester;

[2-(2,5-Dichloro-phenylamino)-4-oxo-4H-thiazol-5-ylidene]-acetic acid methyl ester;

[2-(2,3-Dichloro-phenylamino)-4-oxo-4H-thiazol-5-ylidene]-acetic acid methyl ester;

[2-(2,4,6-Trichloro-phenylamino)-4-oxo-4H-thiazol-5-ylidene]-acetic acid methyl ester;

[2-(2-Chloro-phenylamino)-4-oxo-4H-thiazol-5-ylidene]-acetic acid methyl ester;

[2-(2,6-Dichloro-phenylamino)-4-oxo-4H-thiazol-5-ylidene]-N-(2-methoxy-ethyl)-acetamide;

2-(2,6-Dichloro-phenylamino)-5-(2-oxo-2-piperidine-1-yl-ethylidene)-thiazol-4-one;

2-(2,6-Dichloro-phenylamino)-5-[2-(4-ethyl-piperazin-1-yl)-2-oxo-ethylidene)-thiazol-4-one;

2-[2-(2,6-Dichloro-phenylamino)-4-oxo-4H-thiazol-5-ylidene]-N-(3-pyrrolidin-1-yl-propyl)-acetamide;

2-[2-(2,6-Dichloro-phenylamino)-4-oxo-4H-thiazol-5-ylidene]-N-isopropyl-acetamide;

2-(2,6-Dichloro-phenylamino)-5-(2-oxo-2-pyrrolidin-1-yl-ethylidene)-thiazol-4-one;

N-Cycloheptyl-2-[2-(2,6-dichloro-phenylamino)-4-oxo-4H-thiazol-5-ylidene]-acetamide;

2-[2-(2,6-Dichloro-phenylamino)-4-oxo-4H-thiazol-5-ylidene]-N-(2,2-dimethoxy-ethyl)-acetamide;

2-(2,6-Dichloro-phenylamino)-5-[2-(3,5-dimethyl-piperidin-1-yl)-2-oxo-ethylidene)-thiazol-4-one;

2-(2,6-Dichloro-phenylamino)-5-[2-(3-dimethylamino-pyrrolidin-1-yl)-2-oxo-ethylidene)-thiazol-4-one;

2-[2-(2,6-Dichloro-phenylamino)-4-oxo-4H-thiazol-5-ylidene]-N-[2-(2-hydroxy-ethoxy)-ethyl]-acetamide;

2-[2-(2,6-Dichloro-phenylamino)-4-oxo-4H-thiazol-5-ylidene]-N-(3-methylsulfanyl-propyl)-acetamide;

2-[2-(2,6-Dichloro-phenylamino)-4-oxo-4H-thiazol-5-ylidene]-N-(2,3-dihydroxy-propyl)-acetamide;

2-[2-(2,6-Dichloro-phenylamino)-4-oxo-4H-thiazol-5-ylidene]-N-(2-methyl-allyl)-acetamide;

N-Cyclopentyl-2-[2-(2,6-dichloro-phenylamino)-4-oxo-4H-thiazol-5-ylidene]-acetamide;

N-Cyclopropylmethyl-2-[2-(2,6-dichloro-phenylamino)-4-oxo-4H-thiazol-5-ylidene]-N-propyl-acetamide;

2-[2-(2,6-Dichloro-phenylamino)-4-oxo-4H-thiazol-5-ylidene]-N-methyl-N-(1-methyl-pyrrolidin-3-yl)-acetamide;

2-[2-(2,6-Dichloro-phenylamino)-4-oxo-4H-thiazol-5-ylidene]-N-(2-phenoxy-ethyl)-acetamide;

2-[2-(2,6-Dichloro-phenylamino)-4-oxo-4H-thiazol-5-ylidene]-N-methyl-N-(8-methylamino-octyl)-acetamide;

N-(4-Chloro-benzyl)-2-[2-(2,6-dichloro-phenylamino)-4-oxo-4H-thiazol-5-ylidene]-acetamide;

N-(1-Benzyl-pyrrolidin-3-yl)-2-[2-(2,6-dichloro-phenylamino)-4-oxo-4H-thiazol-5-ylidene]-N-methyl-acetamide;

2-[2-(2,6-Dichloro-phenylamino)-4-oxo-4H-thiazol-5-ylidene]-N-(1,4-dimethyl-pentyl)-acetamide;

2-[2-(2,6-Dichloro-phenylamino)-4-oxo-4H-thiazol-5-ylidene]-N-(1,3-dimethyl-butyl)-acetamide; and N-Cycloheptyl-2-[2-(2,6-dichloro-phenylamino)-4-oxo-4H-thiazol-5-ylidene)-acetamide.

14. A method for inhibiting branched chain amino acid-dependent aminotransferases in a patient, the method comprising the step of administering to the patient a therapeutically effective amount of a compound of claim 1.

15. The method of claim 14, wherein the compound is:

[2-(2,6-Dichloro-phenylamino)-4-oxo-4H-thiazol-5-ylidene]-acetic acid methyl ester;

[2-(2,6-Dichloro-phenylamino)-4-oxo-4H-thiazol-5-ylidene]-acetic acid ethyl ester;

[2-(2,6-Dichloro-phenylamino)-4-oxo-4H-thiazol-5-ylidene]-acetic acid tert-butyl ester;

[2-(2-Methyl-phenylamino)-4-oxo-4H-thiazol-5-ylidene]-acetic acid methyl ester;

[2-(2,6-Dichloro-phenylamino)-4-oxo-4H-thiazol-5-ylidene]-acetic acid;

[2-(2,6-Dichloro-phenylamino)-4-oxo-4H-thiazol-5-ylidene]-N-methyl-acetamide;

[2-(2,6-Dichloro-phenylamino)-4-oxo-4H-thiazol-5-ylidene]-N-ethyl-acetamide;

[2-(2,6-Dichloro-phenylamino)-4-oxo-4H-thiazol-5-ylidene]-N-propyl-acetamide;

[2-(2,6-Dichloro-phenylamino)-4-oxo-4H-thiazol-5-ylidene]-N-benzyl-acetamide;

[2-(2,6-Dichloro-phenylamino)-4-oxo-4H-thiazol-5-ylidene]-N-methoxy-acetamide;

[2-(2,4-Dichloro-phenylamino)-4-oxo-4H-thiazol-5-ylidene]-acetic acid methyl ester;

[2-(2,5-Dichloro-phenylamino)-4-oxo-4H-thiazol-5-ylidene]-acetic acid methyl ester;

[2-(2,3-Dichloro-phenylamino)-4-oxo-4H-thiazol-5-ylidene]-acetic acid methyl ester;

[2-(2,4,6-Trichloro-phenylamino)-4-oxo-4H-thiazol-5-ylidene]-acetic acid methyl ester;

[2-(2-Chloro-phenylamino)-4-oxo-4H-thiazol-5-ylidene]-acetic acid methyl ester;

2-[2-(2,6-Dichloro-phenylamino)-4-oxo-4H-thiazol-5-ylidene]-N-(2-methoxy-ethyl)-acetamide;

2-(2,6-Dichloro-phenylamino)-5-(2-oxo-2-piperidine-1-yl-ethylidene)-thiazol-4-one;

2-(2,6-Dichloro-phenylamino)-5-[2-(4-ethyl-piperazin-1-yl)-2-oxo-ethylidene)-thiazol-4-one;

2-[2-(2,6-Dichloro-phenylamino)-4-oxo-4H-thiazol-5-ylidene]-N-(3-pyrrolidin-1-yl-propyl)-acetamide;

2-[2-(2,6-Dichloro-phenylamino)-4-oxo-4H-thiazol-5-ylidene]-N-isopropyl-acetamide;

2-(2,6-Dichloro-phenylamino)-5-(2-oxo-2-pyrrolidin-1-yl-ethylidene)-thiazol-4-one;

N-Cycloheptyl-2-[2-(2,6-dichloro-phenylamino)-4-oxo-4H-thiazol-5-ylidene]-acetamide;

2-[2-(2,6-Dichloro-phenylamino)-4-oxo-4H-thiazol-5-ylidene]-N-(2,2-dimethoxy-ethyl)-acetamide;

2-(2,6-Dichloro-phenylamino)-5-[2-(3,5-dimethyl-piperidin-1-yl)-2-oxo-ethylidene)-thiazol-4-one;

2-(2,6-Dichloro-phenylamino)-5-[2-(3-dimethylamino-pyrrolidin-1-yl)-2-oxo-ethylidene)-thiazol-4-one;

2-[2-(2,6-Dichloro-phenylamino)-4-oxo-4H-thiazol-5-ylidene]-N-[2-(2-hydroxy-ethoxy)-ethyl]-acetamide;

2-[2-(2,6-Dichloro-phenylamino)-4-oxo-4H-thiazol-5-ylidene)-N-(3-methylsulfanyl-propyl)-acetamide;

2-[2-(2,6-Dichloro-phenylamino)-4-oxo-4H-thiazol-5-ylidene]-N-(2,3-dihydroxy-propyl)-acetamide;

2-[2-(2,6-Dichloro-phenylamino)-4-oxo-4H-thiazol-5-ylidene]-N-(2-methyl-allyl)-acetamide;

N-Cyclopentyl-2-[2-(2,6-dichloro-phenylamino)-4oxo-4H-thiazol-5-ylidene]-acetamide;

N-Cyclopropylmethyl-2-[2-(2,6-dichloro-phenylamino)-4-oxo-4H-thiazol-5-ylidene]-N-propyl-acetamide;

2-[2-(2,6-Dichloro-phenylamino)-4-oxo-4H-thiazol-5-ylidene]-N-methyl-N-(1-methyl-pyrrolidin-3-yl)-acetamide;

2-[2-(2,6-Dichloro-phenylamino)-4-oxo-4H-thiazol-5-ylidene]-N-(2-phenoxy-ethyl)-acetamide;

2-[2-(2,6-Dichloro-phenylamino)-4-oxo-4H-thiazol-5-ylidene]-N-methyl-N-(8-methylamino-octyl)-acetamide;

N-(4-Chloro-benzyl)-2-[2-(2,6-dichloro-phenylamino)-4-oxo-4H-thiazol-5-ylidene]-acetamide;

N-(1-Benzyl-pyrrolidin-3-yl)-2-[2-(2,6-dichloro-phenylamino)-4-oxo-4H-thiazol-5-ylidene]-N-methyl-acetamide;

2-[2-(2,6-Dichloro-phenylamino)-4-oxo-4H-thiazol-5-ylidene]-N-(1,4-dimethyl-pentyl)-acetamide;

2-[2-(2,6-Dichloro-phenylamino)-4-oxo-4H-thiazol-5-ylidene]-N-(1,3-dimethyl-butyl)-acetamide; and N-Cycloheptyl-2-[2-(2,6-dichloro-phenylamino)-4-oxo-4H-thiazol-5-ylidene]-acetamide.

* * * * *